ization="center">United States Patent
Mourich et al.

(10) Patent No.: US 8,415,313 B2
(45) Date of Patent: Apr. 9, 2013

(54) ANTISENSE OLIGOMERS AND METHODS FOR INDUCING IMMUNE TOLERANCE AND IMMUNOSUPPRESSION

(75) Inventors: Dan V. Mourich, Albany, OR (US); Patrick L. Iversen, Corvallis, OR (US); Dwight D. Weller, Corvallis, OR (US)

(73) Assignee: AVI BioPharma, Inc., Corvallis, OR (US)

( * ) Notice: Subject to any disclaimer, the term of this patent is extended or adjusted under 35 U.S.C. 154(b) by 1235 days.

(21) Appl. No.: 11/433,033

(22) Filed: May 11, 2006

(65) Prior Publication Data

US 2006/0276425 A1    Dec. 7, 2006

Related U.S. Application Data

(63) Continuation-in-part of application No. 11/041,164, filed on Jan. 21, 2005, now abandoned.

(60) Provisional application No. 60/538,655, filed on Jan. 23, 2004.

(51) Int. Cl.
| C12N 15/11 | (2006.01) |
| A61K 48/00 | (2006.01) |
| C07H 21/02 | (2006.01) |
| C07H 21/04 | (2006.01) |

(52) U.S. Cl.
USPC ........................................ 514/44 A; 536/24.5

(58) Field of Classification Search .............. 514/44; 435/6, 91.1, 325, 375; 536/23.1, 24.3, 24.33, 536/24.5
See application file for complete search history.

(56) References Cited

U.S. PATENT DOCUMENTS

| 5,034,506 A | 7/1991 | Summerton et al. ........... 528/391 |
| 5,142,047 A | 8/1992 | Summerton et al. ........... 544/118 |

(Continued)

FOREIGN PATENT DOCUMENTS

| WO | 94/26887 | 11/1994 |
| WO | 95/03408 | 2/1995 |

(Continued)

OTHER PUBLICATIONS

Liang et al. (Transplantation, 2003 vol. 76(4):721-729). Administration of dendritic cells transduced with antisense oligodeoxyribnucleotides targeting CD80 or CD86 prolongs allograft survival.*

(Continued)

*Primary Examiner* — Terra Cotta Gibbs
(74) *Attorney, Agent, or Firm* — Seed IP Law Group PLLC

(57) ABSTRACT

A method and composition for inducing human dendritic cells to a condition of reduced capacity for antigen-specific activation of T cells, and, in mature dendritic cells, increased production of extracellular IL-10 is disclosed. A population of dendritic cells is exposed to a substantially uncharged antisense compound, including partially positively charged, containing 12-40 subunits and a base sequence effective to hybridize to a target region within the sequence identified by SEQ ID NO:9, to form a duplex structure between the compound and transcript having a Tm of at least 45° C. Formation of the duplex blocks expression of full-length CD86 in the cells, which in turn leads to reduced capacity for antigen-specific activation of T cells, and, in mature dendritic cells, increased production of extracellular IL-10.

14 Claims, 10 Drawing Sheets

U.S. PATENT DOCUMENTS

| | | | | |
|---|---|---|---|---|
| 5,166,315 | A | 11/1992 | Summerton et al. | 528/406 |
| 5,185,444 | A | 2/1993 | Summerton et al. | |
| 5,217,866 | A | 6/1993 | Summerton et al. | 435/6 |
| 5,506,337 | A | 4/1996 | Summerton et al. | 528/391 |
| 5,521,063 | A | 5/1996 | Summerton et al. | 435/6 |
| 5,580,767 | A | 12/1996 | Cowsert et al. | |
| 5,627,274 | A | 5/1997 | Kole et al. | 536/23.1 |
| 5,665,593 | A | 9/1997 | Kole et al. | 435/375 |
| 5,698,685 | A | 12/1997 | Summerton et al. | 536/24.3 |
| 5,892,023 | A | 4/1999 | Pirotzky et al. | 536/24.5 |
| 5,916,808 | A | 6/1999 | Kole et al. | 435/375 |
| 5,976,879 | A | 11/1999 | Kole et al. | 435/375 |
| 6,319,906 | B1 * | 11/2001 | Bennett et al. | 514/44 A |
| 6,365,351 | B1 | 4/2002 | Iversen | |
| 6,677,153 | B2 | 1/2004 | Iversen | |
| 6,784,291 | B2 | 8/2004 | Iversen et al. | |
| 6,828,105 | B2 | 12/2004 | Stein et al. | |
| 6,841,542 | B2 | 1/2005 | Bartelmez et al. | |
| 7,049,431 | B2 | 5/2006 | Iversen et al. | |
| 7,094,765 | B1 | 8/2006 | Iversen et al. | |
| 7,468,418 | B2 | 12/2008 | Iversen et al. | 530/300 |
| 2003/0220480 | A1 * | 11/2003 | Bonny | 530/350 |
| 2003/0224353 | A1 | 12/2003 | Stein et al. | 435/5 |
| 2004/0265879 | A1 | 12/2004 | Iversen et al. | 435/6 |
| 2005/0234002 | A1 | 10/2005 | Mourich et al. | |
| 2006/0287268 | A1 | 12/2006 | Iversen et al. | 514/44 |
| 2007/0105807 | A1 | 5/2007 | Sazani et al. | 514/44 |
| 2007/0122821 | A1 | 5/2007 | Iversen et al. | 435/6 |
| 2007/0249538 | A1 | 10/2007 | Sazani et al. | 514/12 |
| 2009/0082547 | A1 | 3/2009 | Iversen et al. | 530/322 |
| 2009/0088562 | A1 | 4/2009 | Weller et al. | 536/24.5 |
| 2009/0099066 | A1 | 4/2009 | Moulton et al. | 514/7 |
| 2009/0105139 | A1 | 4/2009 | Kole et al. | 514/12 |
| 2009/0110689 | A1 | 4/2009 | Mourich et al. | 424/184.1 |
| 2009/0246221 | A1 | 10/2009 | Mourich et al. | 424/194.1 |
| 2009/0264353 | A1 | 10/2009 | Orum et al. | 514/12 |
| 2010/0130591 | A1 | 5/2010 | Sazani et al. | 514/44 A |
| 2010/0184670 | A1 | 7/2010 | Mourich et al. | 514/12 |

FOREIGN PATENT DOCUMENTS

| | | |
|---|---|---|
| WO | 97/40854 | 11/1997 |
| WO | 00/74687 | 12/2000 |
| WO | WO01/49775 | 7/2001 |
| WO | 01/72765 | 10/2001 |
| WO | 01/83740 | 11/2001 |
| WO | 2005/000202 | 1/2005 |
| WO | 2006/000057 | 1/2006 |
| WO | 2007/058894 | 5/2007 |
| WO | 2008/051306 | 5/2008 |
| WO | 2008/131807 | 11/2008 |
| WO | 2008/153933 | 12/2008 |
| WO | 2009/086469 | 7/2009 |
| WO | 2010/048586 | 4/2010 |
| WO | 2010/080554 | 7/2010 |

OTHER PUBLICATIONS

Agrawal, S., S. H. Mayrand, et al. (1990). "Site-specific excision from RNA by RNase H and mixed-phosphate-backbone oligodeoxynucleotides.", *Proc Natl Acad Sci USA*, 87(4): 1401-5.

Akhtar, S., et al., *Nucleic Acids Res* 19(20):5551-9, (1991).

Anderson, C. M., et al., *J Neurochem* 73(2):867-73, (1999).

Anderson, K. P., et al., *Antimicrob Agents Chemother*, 40(9):2004-11, (1996).

Bailey, C. P., J. M. Dagle et al. (1998). "Cationic oligonucleotides can mediate specific inhibition of gene expression in *Xenopus oocytes*." *Nucleic Acids Res*, 26(21): 4860-7.

Barawkar, D. A. and T. C. Bruice (1998). "Synthesis, biophysical properties, and nuclease resistance properties of mixed backbone oligodeoxynucleotides containing cationic internucleoside guanidinium linkages: deoxynucleic guanidine/DNA chimeras." *Proc Natl Acad Sci U S A* 95(19): 11047-52.

Blommers, M. J., U. Pieles, et al. (1994). "An approach to the structure determination of nucleic acid analogues hybridized to RNA. NMR studies of a duplex between 2'-OMe RNA and an oligonucleotide containing a single amide backbone modification." *Nucleic Acids Res* 22(20): 4187-94.

Bonham, M. A., S. Brown, et al. (1995). "An assessment of the antisense properties of RNase H-competent and steric-blocking oligomers.", *Nucleic Acids Res* 23(7): 1197-203.

Borriello, F., et al., *J Immunol* 155(12):5490-7, (1995).

Boudvillain, M., M. Guerin, et al. (1997). "Transplatin-modified oligo(2'-O-methyl ribonucleotide)s: a new tool for selective modulation of gene expression." *Biochemistry* 36(10): 2925-31.

Chambers, C. A., et al., *Annu Rev Immunol* 19:565-94, (2001).

Ding, D., et al., *Nucleic Acids Res* 24(2):354-60, (1996).

Gee, J. E., et al., *Antisense Nucleic Acid Drug Dev* 8(2):103-11, (1998).

Gupta, S., *Int J Oncol*, 22(1):15-20, (2003).

Hudziak, R. M., et al., *Antisense Nucleic Acid Drug Dev*, 6(4):267-72, (1996).

Ding, D., S. M. Grayaznov, et al. (1996). "An oligodeoxyribonucleotide N3'→P5' phosphoramidate duplex forms an A-type helix in solution." *Nucleic Acids Res* 24(2): 354-60.

Loke, S. L., et al., *Proc Natl Acad Sci USA*, 86(10):3474-8, (1989).

Lu, W., et al., "Therapeutic dendritic-cell vaccine for chronic HIV-1 infection." *Nat Med*, 10(12):1359-1365 (2004).

Linkletter, B. A. and Bruice, T.C. (2000). "Solid-phase synthesis of positively charged deoxynucleic guanidine (DNG) modified oligonucleotides containing neutral urea linkages: Effect of charge deletions on binding and fidelity." *Bioorg. Med. Chem.*, 8(11): 1893-1901.

Micklefield, J. (2001). "Backbone modification of nucleic acids: synthesis, structure and therapeutic applications." *Curr Med Chem.*, 8(10): 1157-79.

Moulton, H. M., et al., *Antisense Nucleic Acid Drug Dev.*, 13(1):31-43, (2003).

Moulton, H. M. and J. D. Moulton, *Curr Opin Mol Ther*. 5(2):123-32, (2003).

Moulton, H. M., M. H. Nelson, et al. (2004). "Cellular uptake of antisense morpholino oligomers conjugated to arginine-rich peptides.", *Bioconjug Chem* 15(2): 290-9.

Mohamadzadeh, M. and R. Luftig, *J Immune Based Ther Vaccines* 2(1):1, (2004).

Nelson, M. H., D. A. Stein, et al. (2005). "Arginine-rich peptide conjugation to morpholino oligomers: effects on antisense activity and specificity.", *Bioconjug Chem*, 16(4): 959-66.

Orabona, C., et al., "CD28 induces immunostimulatory signals in dendritic cells via CD80 and CD86." 5(11):1134-1142, (2004).

Pari, G. S., et al., *Antimicrob Agents Chemother*, 39(5):1157-61, (1995).

Salomon, B. and J. A. Bluestone, *Annu Rev Immunol*, 19:225-52, (2001).

Shevac, E. M., "Animal Models for Autoimmune and Inflammatory Disease", *Current Protocols in Immunology*, John Wiley & Sons, Inc., S52, (2002).

Stein, D., et al., *Antisense Nucleic Acid Drug Dev*, 7(3):151-7, (1997).

Summerton et al., *Antisense & Nucleic Acid Drug Development*, 7:63-70 (1997).

Summerton, J. and D. Weller (1997). "Morpholino antisense oligomers: design, preparation, and properties." *Antisense Nucleic Acid Drug Dev*, 7(3):187-95.

Toulme, J. J., R. L. Tinevez, et al. (1996). "Targeting RNA structures by antisense oligonucleotides." *Biochimie*, 78(7): 663-73.

Van der Merwe, P. A. and S. J. Davis, *Annu Rev Immunol*, 21:659-84, (2003).

Wasem, C., et al., *J Clin Invest*, 111(8):1191-9, (2003).

Wender, P. A., et al., *Proc Nat Acad Sci USA*, 97(24):13003-8, (2000).

Yakubov, L. A., et al., *Proc Natl Acad Sci USA*, 86(17):6454-8, (1989).

Liang, X. et al., "Administration of dendritic cells transduced with antisense oligodeoxyribonucleotides targeting CD80 or CD86 prolongs allograft survival", *Transplantation.*, 76 4):721-729 (2003).

Chen et al., "A Concise Method for the Preparation of Peptide and Arginine-Rich Peptide-Conjugated Antisense Oligonucleotide" *Bioconjugate Chem.* 14:532-538, 2003.

Hase et al., "Compositions for Enhancing Transport of Molecules Into Cells" U.S. Appl. No. 60/466,703, filed Apr. 29, 2003, 55 pages.

Hinrichs et al., "Antisense Compound and Method for Selectively Killing Activated T Cells" U.S. Appl. No. 60/505,418, filed Sep. 23, 2003, 60 pages.

International Search Report for Application No. PCT/AU2005/000943, mailed Oct. 20, 2005, 5 pages.

International Search Report for Application No. PCT/EP2007/061211, mailed Dec. 18, 2008, 7 pages.

International Search Report for Application No. PCT/US1994/005181, mailed Oct. 7, 1994, 3 pages.

International Search Report for Application No. PCT/US1999/022448, mailed Dec. 23, 1999, 1 page.

International Search Report for Application No. PCT/US2000/008174, mailed Jul. 25, 2000, 2 pages.

International Search Report for Application No. PCT/US2001/014410, mailed Mar. 6, 2002, 5 pages.

International Search Report for Application No. PCT/US2006/043651, mailed Jun. 27, 2007, 8 pages.

International Search Report for Application No. PCT/US2007/010556, mailed Mar. 13, 2008, 7 pages.

International Search Report for Application No. PCT/US2008/088339, mailed Jun. 4, 2009, 4 pages.

International Search Report for Application No. PCT/US2009/061960, mailed Apr. 6, 2010, 7 pages.

International Search Report for Application No. PCT/US2009/068599, mailed May 21, 2010, 3 pages.

Iversen, "Phosphorodiamidate morpholino oligomers: Favorable properties for sequence-specific gene inactivation" Current Opinion in Molecular Therapeutics 3(3):235-238, 2001.

Liang et al., "Phenotype and Allostimulatory Function of Dendritic Cells Treated with Antisense Oligodeoxyribonucleotides Targeting CD80 or CD86 mRNA" Transplantation Proceedings 33:235, 2001.

Lu et al., "Regulation of self-tolerance by CD80/CD86 interactions" Current Opinion in Immunology 9:858-862, 1997.

Moulton et al., "Compound and Method for Treating Myotonic Dystrophy" U.S. Appl. No. 12/493,140, filed Jun. 26, 2009, 100 pages.

Sansom et al., "What's the difference between CD80 and CD86?" Trends in Immunology 24(6):313-318, 2003.

Wilton et al., "Antisense Oligonucleotides for Inducing Exon Skipping and Methods of Use Thereof" U.S. Appl. No. 11/570,691, filed Jan. 15, 2008, 117 pages.

Wilton et al., "Antisense Oligonucleotides for Inducing Exon Skipping and Methods of Use Thereof" U.S. Appl. No. 12/837,356, filed Jul. 15, 2010, 88 pages.

Wilton et al., "Antisense Oligonucleotides for Inducing Exon Skipping and Methods of Use Thereof" U.S. Appl. No. 12/837,359, filed Jul. 15, 2010, 88 pages.

Wilton et al., "Antisense Oligonucleotdies for Inducing Exon Skipping and Methods of Use Thereof" U.S. Appl. No. 12/860,078, filed Aug. 20, 2010, 88 pages.

Asadullah et al., "Interleukin-10 Therapy-Review of a New Approach" Pharmacological Reviews 55(2):241-269, 2003.

Jiang et al., "Secretion of interleukin-10 or interleukin-12 by LPS-activated dendritic cells is critically dependent on time of stimulus relative to initiation of purified DC culture" Journal of Leukocyte Biology 72:978-985, 2002.

Agrawal et al., "Oligodeoxynucleoside phosphoramidates and phosphorothioates as inhibitors of human immunodeficiency virus," *Proc. Natl. Acad. Sci. USA 85*:7079-7083, 1988.

Asadullah et al., "Interleukin-10 Therapy-Review of a New Approach," *Pharmacological Reviews 55*(2):241-269, 2003.

ATCC Catalog p. IC-21 Cells, downloaded Jan. 19, 2011, http://www.atcc.org/ATCCAdvancedCatalogSearch/ProductDetails/tabid/452/Default.aspx.

Geller et al., "Antisense Antibacterial Method and Compound," Office Action mailed Sep. 29, 2010, U.S. Appl. No. 11/173,847, 25 pages Iversen et al., "Splice-Region Antisense Composition and Method," Office Action mailed on Apr. 23, 2010, U.S. Appl. No. 11/433,214, 17 pages.

Iversen et al., "Antisense Antiviral Compound and Method for Treating ssRNA Viral Infection," Office Action mailed Oct. 9, 2010, U.S. Appl. No. 11/432,031, 25 pages.

Jiang et al., "Secretion of interleukin-10 or interleukin-12 by LPS-activated dendritic cells is critically dependent on time of stimulus relative to initiation of purified DC culture," *Journal of Leukocyte Biology 72*:978-985, 2002.

Stein et al., "Antisense Antiviral Agent and Method for Treating ssRNA Viral Infection," Office Action mailed Feb. 17, 2010, U.S. Appl. No. 11/431,968, 19 pages.

Weller et al., "Oligonucleotide Analogs Having Cationic Intersubunit Linkages," Office Action mailed Aug. 18, 2010, U.S. Appl. No. 11/801,885, 6 pages.

Weller et al., "Oligonucleotide Analogs Having Cationic Intersubunit Linkages," Advisory Action mailed Oct. 28, 2010, U.S. Appl. No. 11/801,885, 6 pages.

* cited by examiner

P002 = N-RRRQRRKKRGYC-CONH$_2$ (SEQ ID NO:1)
P003 = N-RRRRRRRRRFFC-CONH$_2$ (SEQ ID NO:2)
P005 = N-RRRQRRKKRGYFFC-CONH$_2$ (SEQ ID NO:3)

| Treatment | % DCs CD86 Positive | % DCs IL10 Positive |
|---|---|---|
| Control (No LPS) | 6.92 | 0.10 |
| P002 Peptide (No LPS) | 6.47 | 0.10 |
| Scramble-P002 + LPS | 13.4 | 0.75 |
| CD86(AUG)-P002 (SEQ ID NO:??)+LPS | 2.26 | 21.1 |
Fig. 7A
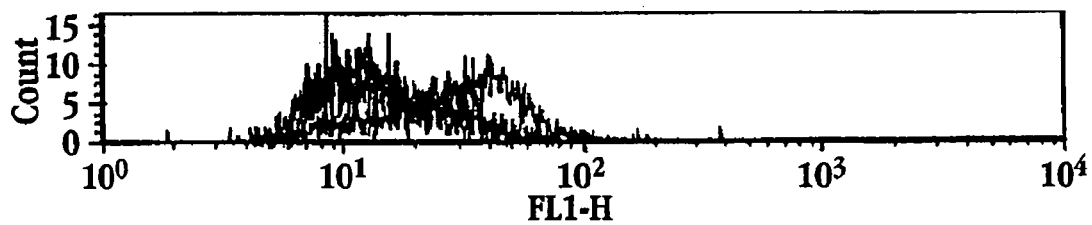
Fig. 7B
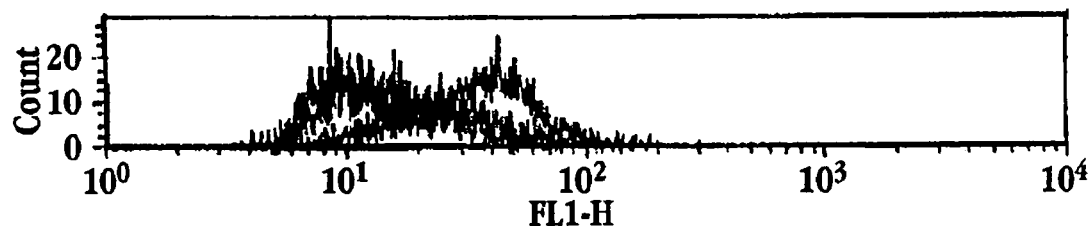
Fig. 7C
IL-10
Fig. 7D

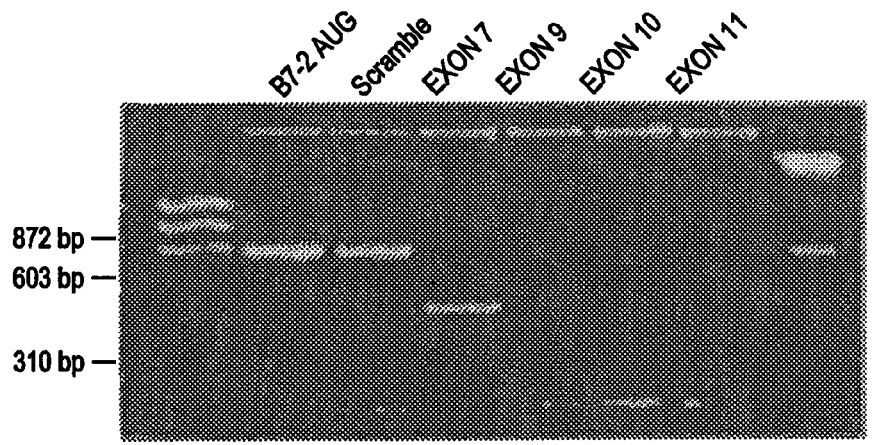
Fig. 8A
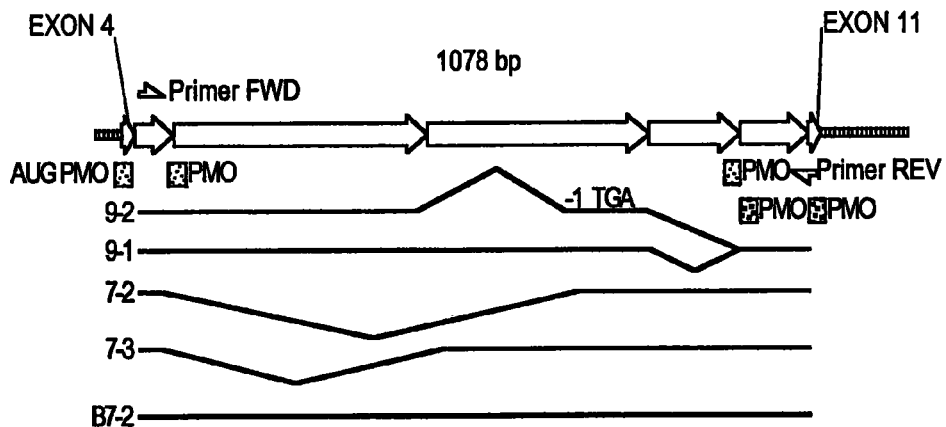
Fig. 8B
| Treatment | % DCs CD86 Positive | % DCs IL10 Positive |
|---|---|---|
| Control | 10.40 | 0.30 |
| Control (+ LPS) | 33.81 | 0.07 |
| CD86-AUG (SEQ ID NO:??) +LPS | 17.93 | 2.06 |
| EXON 9 (SEQ ID NO:??) +LPS | 26.62 | 1.48 |
| EXON 10 (SEQ ID NO:??) +LPS | 13.36 | 4.04 |
| EXON 11 (SEQ ID NO:??) +LPS | 5.06 | 0.65 |
Fig. 8C

ANTISENSE OLIGOMERS AND METHODS FOR INDUCING IMMUNE TOLERANCE AND IMMUNOSUPPRESSION

This application is a continuation-in-part of U.S. patent application Ser. No. 11/041,164, filed Jan. 21, 2005, now abandoned, which claims the benefit of priority to U.S. Provisional Application No. 60/538,655, filed Jan. 23, 2004. Both applications are incorporated herein by reference in their entirety.

FIELD OF THE INVENTION

The present invention relates to compounds and methods of inducing immunological tolerance using a peptide-antisense conjugate to selectively limit costimulation of naïve T-cells by mature dendritic cells and formation of a cytokine microenvironment that augments tolerized T-cells.

REFERENCES

Agrawal, S., et al., *Proc Natl Acad Sci USA* 87(4):1401-5, (1990).
Akhtar, S., et al., *Nucleic Acids Res* 19(20):5551-9, (1991).
Anderson, C. M., et al., *J Neurochem* 73(2):867-73, (1999).
Anderson, K. P., et al., *Antimicrob Agents Chemother* 40(9): 2004-11, (1996).
Bonham, M. A., et al., *Nucleic Acids Res* 23(7):1197-203, (1995).
Borriello, F., et al., *J Immunol* 155(12):5490-7, (1995).
Boudvillain, M., et al., *Biochemistry* 36(10):2925-31, (1997).
Chambers, C. A., et al., *Annu Rev Immunol* 19:565-94, (2001).
Ding, D., et al., *Nucleic Acids Res* 24(2):354-60, (1996).
Gee, J. E., et al., *Antisense Nucleic Acid Drug Dev* 8(2):103-11, (1998).
Gupta, S., *Int J Oncol* 22(1):15-20, (2003).
Hudziak, R. M., et al., *Antisense Nucleic Acid Drug Dev* 6(4):267-72, (1996).
Loke, S. L., et al., *Proc Natl Acad Sci USA* 86(10):3474-8, (1989).
Lu, W., et al., "Therapeutic dendritic-cell vaccine for chronic HIV-1 infection." *Nat Med*, (2004).
Mohamadzadeh, M. and R. Luftig, *J Immune Based Ther Vaccines* 2(1): 1, (2004).
Moulton, H. M., et al., *Antisense Nucleic Acid Drug Dev* 13(1):31-43, (2003).
Moulton, H. M. and J. D. Moulton, *Curr Opin Mol Ther* 5(2):123-32, (2003).
Moulton, H. M., et al., *Bioconjug Chem* 15(2):290-9, (2004).
Orabona, C., et al., "CD28 induces immunostimulatory signals in dendritic cells via CD80 and CD86." 5(11):1134-1142, (2004).
Pari, G. S., et al., *Antimicrob Agents Chemother* 39(5):1157-61, (1995).
Salomon, B. and J. A. Bluestone, *Annu Rev Immunol* 19:225-52, (2001).
Shevac, E. M., "Animal Models for Autoimmune and Inflammatory Disease", *CURRENT PROTOCOLS IN IMMUNOLOGY*, John Wiley & Sons, Inc., S52, (2002).
Stein, D., et al., *Antisense Nucleic Acid Drug Dev* 7(3):151-7, (1997).
Summerton, J. and D. Weller, *Antisense Nucleic Acid Drug Dev* 7(3):187-95, (1997).
Toulme, J. J., et al., *Biochimie* 78(7):663-73, (1996).
van der Merwe, P. A. and S. J. Davis, *Annu Rev Immunol* 21:659-84, (2003).
Wasem, C., et al., *J Clin Invest* 111(8):1191-9, (2003).
Wender, P. A., et al., *Proc Natl Acad Sci USA* 97(24):13003-8, (2000).
Yakubov, L. A., et al., *Proc Natl Acad Sci USA* 86(17):6454-8, (1989).

BACKGROUND OF THE INVENTION

Transplantation of allogeneic donor cells, tissues or organs (transplantation between genetically different individuals of the same species) is used to treat a variety of conditions (typically tissue, or organ-failure conditions) and is often the sole or highly preferred therapeutic option. The list of successfully transplanted cells, tissues and organs includes kidney, heart, lung, liver, corneas, pancreas, marrow, skin, and bones. However, allogeneic transplantation involves significant risks and drawbacks, including graft rejection, complications from immunosuppressive therapy and graft-versus host disease which are frequently highly debilitating or lethal.

Rejection of allografts is presently understood to be initiated by the recognition of allogeneic (i.e. donor) major histocompatibility complex (MHC) molecules by recipient T-lymphocytes, leading to upregulated cellular and humoral immunity through activation of T cells. The MHC antigens are typically presented to the recipient T-lymphocytes by antigen presenting cells, such as macrophages and dendritic cells. Although immunosuppressive drugs such as cyclosporine may be used in an attempt to modulate rejection, these immunosuppressive agents have severe side effects and often fail to prevent continued rejection episodes.

Dendritric cells (DCs) are a family of professional antigen presenting cells (APCs) that are present in virtually all tissues of the body. The ability of dendritic cells to capture foreign antigens, migrate to lymphoid tissues and redistribute antigen-MHC to the cell surface along with appropriate costimulatory signals are well known T-cell priming functions for these APCs. In addition to these immunostimulatory properties, dendritic cells are also known to play a role in down-regulating immune responses. Certain subpopulations of dendritic cells, acting as professional APCs, also maintain and regulate T-cell tolerance in the periphery. There is thus a need for therapeutic methods and compositions capable of inducing immunological tolerance with lower toxicity and improved efficacy.

SUMMARY OF THE INVENTION

The invention includes, in one aspect, a method of inducing human dendritic cells to a condition of reduced capacity for antigen-specific activation of T cells, and, in mature dendritic cells, increased production of extracellular IL-10. The method includes exposing a population of human dendritic cells to a substantially uncharged antisense compound containing 12-40 subunits and a base sequence effective to hybridize to an expression-sensitive region of a preprocessed or processed human CD-86 transcript identified, in its processed form, by SEQ ID NO:33, to form, between the compound and transcript, a heteroduplex structure having a Tm of at least 45° C. The heteroduplex formation blocks expression of full-length CD86 in the cells, which in turn, produces inhibition of the expression of full-length CD86 on the surface of dendritic cells, and produces enhanced expression of extracellular IL-10 by mature dendritic cells.

In a preferred embodiment, the antisense compound to which the dendritic cells are exposed is composed of phosphorus-containing intersubunit linkages joining a morpholino nitrogen of one subunit to a 5' exocyclic carbon of an adjacent subunit. In an exemplary compound, the morpholino subunits in the compound are joined by phosphorodiamidate linkages, in accordance with the structure:

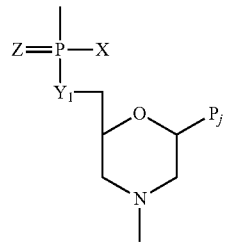

where $Y_1=O$, $Z=O$, Pj is a purine or pyrimidine base-pairing moiety effective to bind, by base-specific hydrogen bonding, to a base in a polynucleotide, and X is alkyl, alkoxy, thioalkoxy, amino or alkyl amino, and the heteroduplex structure formed has a Tm of at least 50° C. For example, $X=NR_2$, where each R is independently hydrogen or methyl in the compound to which the dendritic cells are exposed. The compound may be composed of morpholino subunits linked with the uncharged linkages described above interspersed with linkages that are positively charged at physiological pH. The total number of positively charged linkages is between 2 and no more than half of the total number of linkages. The positively charged linkages have the structure above, where X is 1-piperazine.

The compound may be covalently linked, at one compound end, to an arginine-rich peptide effective to enhance uptake of the compound into the dendritic cells. Exemplary arginine-rich peptides are those having the sequences SEQ ID NOS: 1 or 2. Where the dendritic cells include a mixture of immature and mature dendritic cells, the arginine-rich peptide may be an rTAT peptide having the sequence identified by SEQ ID NO: 1. This peptide is effective to achieve a greater level of intracellular uptake of the antisense compound into the mature dendritic cells than is achieved (i) in the immature dendritic cells, or (ii) by exposing the mature dendritic cells to the antisense compound in the absence of the rTAT polypeptide.

More generally, the rTAT peptide may be coupled to any antisense or other therapeutic compound to achieve selective uptake of the compound into mature dendritic cells, relative to uptake in immature cells.

Where the antisense compound is effective to hybridize to an expression-sensitive target region adjacent the start site of the processed human CD86 transcript, the compound may have a base sequence that is complementary to a target region containing at least 12 contiguous bases in a processed human CD86 transcript identified by SEQ ID NO:9, where the compound is effective to block translation of the processed transcript. The antisense compound may have, for example, one of the base sequence identified by SEQ ID NOS:21-23 and 32.

Where the antisense compound is effective to hybridize to a splice site of preprocessed human CD86, the compound may have a base sequence that is complementary to at least 12 contiguous bases of a splice site in a preprocessed human CD86 transcript, where the compound is effective to block processing of a preprocessed CD86 transcript to produce a full-length, processed CD 86 transcript. The splice site in the preprocessed CD86 transcript may have one of the sequences identified by SEQ ID NOS:10-14. The antisense compound may have, for example, one of the base sequences identified by SEQ ID NOS:24-28.

For use in inhibiting transplantation rejection in a human subject receiving an allograft tissue or organ, the compound is administered to the subject in an amount effective to inhibit the rate and extent of rejection of the transplant. The compound may be administered both prior to and following the allograft tissue or organ transplantation in the subject, and compound administration may be carried out for a selected period of 1-3 weeks. The compound may be further administered to the subject, as needed, to control the extent of transplantation rejection in the subject.

For use in treating an autoimmune condition in a human subject, the compound may be administered to the subject, in an amount effective to reduce the severity of the autoimmune condition. The compound may be administered over an extended period of time, as needed, to control the severity of the autoimmune condition in the subject.

In another aspect, the invention provides a composition for use in inducing dendritic cells to a condition of reduced capacity for antigen-specific activation of T cells, and, in mature dendritic cells, increased production of extracellular IL-10. The compound comprises a substantially uncharged antisense compound containing 12-40 subunits and a base sequence effective to hybridize to an expression-sensitive region of a preprocessed or processed human CD-86 transcript identified, in its processed form, by SEQ ID NO:33, to form a heteroduplex structure between said compound and transcript having a Tm of at least 45° C. Exemplary features of the compound are as described above.

These and other objects and features of the invention will become more fully apparent when the following detailed description of the invention is read in conjunction with the accompanying drawings.

BRIEF DESCRIPTION OF THE FIGURES

FIGS. 7A-7D demonstrate that blocking CD86 interactions do not lead to IL-10 induction in dendritic cells.

FIG. 8A-8C show that antisense PMO targeting of splice donor or acceptor sites alters CD86 mRNA.

DETAILED DESCRIPTION OF THE INVENTION

I. Definitions

Figure 1A:
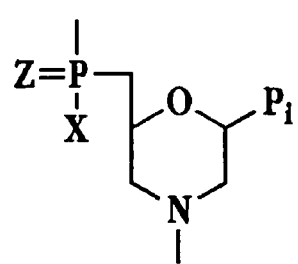
FIGS. 1A-1D show several preferred morpholino-type subunits having 5-atom (A), six-atom (B) and seven-atom (C-D) linking groups suitable for forming polymers.

The terms below, as used herein, have the following meanings, unless indicated otherwise.

The terms "CD80" and "CD86" refer to the costimulatory protein molecules that are expressed on the surface of mature, antigen presenting dendritic cells. T cell activation is dependent upon signals delivered through the antigen-specific T cell receptor and accessory costimulatory receptors on the T cell. The CD28 costimulatory receptor is constitutively expressed on T cells. Engagement of CD28 on naïve T cells by either CD80 or CD86 ligands on antigen presenting cells (e.g. mature dendritic cells) provides a potent costimulatory signal to T cells activated through their T cell receptor. The CD80 and CD86 costimulatory molecules are also known as B7-1 and B7-2, respectively. The term "B7 molecules" refer collectively to the CD80 and CD86 molecules.

The term "antigen-activated T cells" refers to T cells that become activated after the T cell receptor (TCR) complex and a co-stimulatory receptor (e.g. CD28 on naïve CD4 and CD8 T cells) are engaged to the extent that a signal transduction cascade is initiated. Antigen is bound by the TCR in the form of a foreign peptide in the context of a self MHC molecule, either Class I or Class II, in the case of CD4 and CD8 T cells respectively, conferring the antigen specificity of the T cell. Upon activation, T cells will proliferate and then secrete cytokines or carry out cytolysis on cells expressing the foreign peptide with self MHC. Cytokines are growth factors for other T cells or signals for B cells to produce antibody.

The term "antigen-activated B cells" refer to either of two different types of B cell activation, T cell dependent and T cell independent. T cell independent antigens contain repetitive identical epitopes and are capable of clustering membrane bound antibody on the surface of the B cell which can result in delivering activation signals. T cell dependent activation is in response to protein antigens where the B cell acts as a professional antigen presenting cell. Surface antibody bound to antigen is internalized by the B cell, the antigen processed and presented as peptides on the B cell surface bound to MHC II molecules. Responding T cells recognize the peptide as foreign in the context of self MHC and respond by secreting cytokines and expression of CD40L. Together these provide a co-stimulatory signal to the B cell. In either case of B cell activation the cell will proliferate and differentiate into plasma B cells capable of secreting antibodies against the antigen.

The terms "activated dendritic cells" and "mature dendritic cells" (DCs) refer to professional antigen-presenting cells (APCs) capable of expressing both MHC class I and II and co-stimulatory molecules including CD80 (B7-1) and CD86 (B7-2). Two different DC phenotypes are exhibited depending on maturation state and location in the body. Immature DCs reside in all tissues and organs as active phagocytic cells. Mature DCs traffic to secondary lymphoid organs (e.g. lymph node and spleen) and present peptides derived from processed protein antigens to T cells in the context of MHC molecules. Mature DCs also provide the necessary co-stimulatory signals to T cells by expressing the appropriate surface ligand (e.g. CD80 and CD86 on DCs bind to CD28 on T cells).

The terms "antisense oligonucleotides," "antisense oligomer," and "antisense compound" are used interchangeably and refer to a compound having a sequence of nucleotide bases and a subunit-to-subunit backbone that allows the antisense oligomer to hybridize to a target sequence in an RNA by Watson-Crick base pairing, to form an RNA:oligomer heteroduplex within the target sequence. The antisense oligonucleotide includes a sequence of purine and pyrimidine heterocyclic bases, supported by a backbone, which are effective to hydrogen-bond to corresponding, contiguous bases in a target nucleic acid sequence. The backbone is composed of subunit backbone moieties supporting the purine and pyrimidine heterocyclic bases at positions that allow such hydrogen bonding. These backbone moieties are cyclic moieties of 5 to 7 atoms in length, linked together by phosphorous-containing linkages one to three atoms long.

A "morpholino" oligonucleotide refers to a polymeric molecule having a backbone which supports bases capable of hydrogen bonding to typical polynucleotides, wherein the polymer lacks a pentose sugar backbone moiety, and more specifically a ribose backbone linked by phosphodiester bonds which is typical of nucleotides and nucleosides, but instead contains a ring nitrogen with coupling through the ring nitrogen. A preferred "morpholino" oligonucleotide is composed of morpholino subunit structures of the form shown in FIG. 1A-1D, where (i) the structures are linked together by phosphorous-containing linkages, one to three atoms long, joining the morpholino nitrogen of one subunit to the 5' exocyclic carbon of an adjacent subunit, and (ii) Pi and Pj are purine or pyrimidine base-pairing moieties effective to bind, by base-specific hydrogen bonding, to a base in a polynucleotide. Exemplary structures for antisense oligonucleotides for use in the invention include the morpholino subunit types shown in FIGS. 1A-1D, with the uncharged, phosphorous-containing linkages shown in FIGS. 2A-2D, and more generally, the uncharged linkages 3A-3G.

A substantially uncharged, phosphorus containing backbone in an oligonucleotide analog is one in which a majority of the subunit linkages, e.g., between 50-100%, are uncharged at physiological pH, and contain a single phosphorous atom. The analog contains between 12 and 40 subunits, typically about 15-25 subunits, and preferably about 18 to 25 subunits. The analog may have exact sequence complementarity to the target sequence or near complementarity, as defined below.

A "subunit" of an oligonucleotide analog refers to one nucleotide (or nucleotide analog) unit of the analog. The term may refer to the nucleotide unit with or without the attached intersubunit linkage, although, when referring to a "charged subunit", the charge typically resides within the intersubunit linkage (e.g. a phosphate or phosphorothioate linkage).

A preferred morpholino oligomer is a phosphorodiamidate-linked morpholino oligomer, referred to herein as a PMO. Such oligomers are composed of morpholino subunit structures such as shown in FIG. 2B, where X=NH2, NHR, or NR2 (where R is lower alkyl, preferably methyl), Y=O, and Z=O, and Pi and Pj are purine or pyrimidine base-pairing moieties effective to bind, by base-specific hydrogen bonding, to a base in a polynucleotide, as seen in FIG. 2E. Also preferred are morpholino oligomers where the phosphordiamidate linkages are uncharged linkages as shown in FIG. 3G interspersed with cationic linkages as shown in FIG. 3H where, in FIG. 2B, X=1-piperazino. In another FIG. 2B embodiment, X=lower alkoxy, such as methoxy or ethoxy, Y=NH or NR, where R is lower alkyl, and Z=O.

As used herein, an oligonucleotide or antisense oligomer "specifically hybridizes" to a target polynucleotide if the oligomer hybridizes to the target under physiological conditions, with a thermal melting point (Tm) substantially greater than 37° C., preferably at least 45° C., and typically 50° C.-80° C. or higher. Such hybridization preferably corresponds to stringent hybridization conditions, selected to be about 10° C., and preferably about 50° C. lower than the Tm for the specific sequence at a defined ionic strength and pH. At a given ionic strength and pH, the Tm is the temperature at which 50% of a target sequence hybridizes to a complementary polynucleotide.

Polynucleotides are described as "complementary" to one another when hybridization occurs in an antiparallel configuration between two single-stranded polynucleotides. A double-stranded polynucleotide can be "complementary" to another polynucleotide, if hybridization can occur between one of the strands of the first polynucleotide and the second. Complementarity (the degree that one polynucleotide is complementary with another) is quantifiable in terms of the proportion of bases in opposing strands that are expected to form hydrogen bonds with each other, according to generally accepted base-pairing rules. An antisense compound may be complementary to a target region of a target transcript even if the two bases sequences are not 100% complementary, as long as the heteroduplex structure formed between the compound and transcript has the desired Tm stability.

As used herein the term "analog" with reference to an oligomer means a substance possessing both structural and chemical properties similar to those of the reference oligomer.

As used herein, a first sequence is an "antisense sequence" or "targeting sequence" with respect to a second sequence or "target sequence" if a polynucleotide whose sequence is the first sequence specifically binds to, or specifically hybridizes with, the second polynucleotide sequence under physiological conditions.

As used herein, "effective amount" relative to an antisense oligomer refers to the amount of antisense oligomer administered to a subject, either as a single dose or as part of a series of doses, that is effective to inhibit expression of a selected target nucleic acid sequence.

As used herein, an "expression-sensitive region" of a processed or preprocessed mRNA transcript refers to either (i) a region including or adjacent the AUG start site of a processed transcript, where formation of an antisense-transcript heteroduplex is effective to inhibit translation of the transcript or (ii) a region including or adjacent a donor or acceptor splice site junction in a preprocessed transcript, where formation of an antisense-transcript heteroduplex is effective to inhibit formation of a full-length processed transcript, either because one or more exons that would normally be included in the transcript have been deleted or because the transcript has been truncated at the target splice site.

"Dendritic cells" are specialized antigen presenting cells (APCs) with potent capacity to initiate and direct the antigen-specific responses of naïve T cells. This heterogeneous population of cells reside in blood and all tissues as two phenotypically and functionally distinct forms. "Immature DCs" are highly phagocytic, proficient for antigen processing and characterized by low-level expression of major histocompatibility complex (MHC) class II and T cell costimulatory ligands of the B7 family, CD80 and CD86. Maturation can be triggered by various stimuli derived from either host or pathogen. In response to such stimuli, "mature DCs" cease phagocytic activity and significantly increase surface expression of MHC 11, CD80 and CD86. Consequently mature DCs are capable of providing sufficient ligand to trigger T cell activation through the T cell and costimulatory receptors.

Abbreviations:
PMO=phosphorodiamidate morpholino oligomer
AICD=activation induced cell death
MHC=major histocompatibility
TCR=T cell receptor
DC=dendritic cell
APC=antigen presenting cell II. The Role of Antigen Presenting Cells in Transplantation and Autoimmune Disorders There is evidence from the two signal model for T cell activation that costimulation by the engagement of dendritic-cell CD86 molecules with CD28 on T cells is necessary for the complete induction of T cell responses. The process of antigen presentation whereby MHC plus peptide antigen are presented by the dendritic cell to the T cell receptor (TCR) is termed "signal 1". In circumstances where there is either insufficient or an absence of costimulation (termed "signal 2") during the process of antigen presentation, antigen specific tolerance can occur.

Tolerance produced by a loss in signal 2 can be a result of clonal deletion (T cell death in the population of cells recognizing signal 1), anergy (non-responsiveness in the antigen-specific population on subsequent encounters) or through the generation of a regulatory population of antigen-specific T cells. Regulatory T cells can be induced through the presentation of antigen by immature dendritic cells which express reduced levels of CD86 compared to mature dendritic cells. Regulatory T cells provide a form of functional tolerance whereby they produce inhibitory cytokines (IL4, IL-10, and TGF-beta) when encountering antigen and thus inhibit the organism from responding to the antigen (i.e., immuno-suppression). It has been shown that the process of generating T regulatory cells can be further facilitated by providing a third signal ("signal 3") that is the type of cytokines produced by the antigen presenting cell while providing signal 1 and 2.

IL-10, previously termed "cytokine synthesis inhibiting factor" due to its ability to inhibit cytokine production of most immune cell types, can provide a signal 3 to T cells. During the early stages of T cell activation, upon responding to antigen, the cytokines produced by the dendritic cell presenting antigen will promote the resulting phenotype of the responding T cell. IL-12 and IL-4 produced by dendritic cells promote T cell responses of the Th1 and Th2 phenotypes, respectively. The T cell types in turn direct the production of cytotoxic T cells or antibodies, respectively, which are effector cells and molecules capable of rejecting transplants or producing autoimmune disease. Th3 T cells exhibit a regulatory phenotype that directly inhibits the development of any future T cell responses from becoming either a Th1 or Th2 cell capable of responding to the antigen recognized by the Th3 cell or the newly responding T cells. Dendritic cells producing IL-10 can thus induce a tolergenic response by diverting the development of T cell responses from Th1 and Th2 to a Th3 T cell type.

The present invention provides a means to precisely and specifically alter the manner in which dendritic cells elicit antigen-specific immune responses from T cells. In particular a diminution in the level of CD86 protein is achieved by antisense inhibition targeted to dendritic cells. Experiments conducted in support of the invention demonstrated that maturing DCs produce increased amounts of IL-10 as a result of diminished CD86 expression. Moreover, it was determined that the cytoplasmic region encoded by exon 10 is functionally linked to the regulation of this cytokine.

III. Antisense Compound for Targeting Activated Immune Cells

A. Antisense Compound

Antisense oligomers for use in practicing the invention preferably have the following properties: (1) a backbone that is substantially uncharged, (2) the ability to hybridize with the complementary sequence of a target RNA with high affinity, that is a Tm substantially greater than 37° C., preferably at least 45° C., and typically greater than 50° C., e.g., 60° C.-80° C. or higher, (3) a subunit length of at least 8 bases, generally about 8-40 bases, preferably 12-25 bases, and (4) nuclease resistance. In addition, the antisense compound may have the capability for active or facilitated transport as evidenced by (i) competitive binding with a phosphorothioate antisense oligomer, and/or (ii) the ability to transport a detectable reporter into target cells.

Candidate antisense oligomers may be evaluated, according to well known methods, for acute and chronic cellular toxicity, such as the effect on protein and DNA synthesis as measured via incorporation of 3H-leucine and 3H-thymidine, respectively. In addition, various control oligonucleotides, e.g., control oligonucleotides such as sense, nonsense or scrambled antisense sequences, or sequences containing mismatched bases, in order to confirm the specificity of binding of candidate antisense oligomers. The outcome of such tests is important in discerning specific effects of antisense inhibition of gene expression from indiscriminate suppression. Accordingly, sequences may be modified as needed to limit non-specific binding of antisense oligomers to non-target nucleic acid sequences.

Heteroduplex formation. The effectiveness of a given antisense oligomer molecule in forming a heteroduplex with the target mRNA may be determined by screening methods known in the art. For example, the oligomer is incubated in a cell culture containing an mRNA preferentially expressed in activated lymphocytes, and the effect on the target mRNA is evaluated by monitoring the presence or absence of (1) heteroduplex formation with the target sequence and non-target sequences using procedures known to those of skill in the art, (2) the amount of the target mRNA expressed by activated lymphocytes, as determined by standard techniques such as RT-PCR or Northern blot, (3) the amount of protein transcribed from the target mRNA, as determined by standard techniques such as ELISA or Western blotting. (See, for example, (Pari, Field et al. 1995; Anderson, Fox et al. 1996). For the purposes of the invention, a preferred test for the effectiveness of the CD86 antisense oligomer is by measuring the induction of IL-10 expression and loss of CD86 expression in mature dendritic cells treated with a CD86 PMO antisense compound.

Uptake into cells. A second test measures cell transport, by examining the ability of the test compound to transport a labeled reporter, e.g., a fluorescence reporter, into cells. The cells are incubated in the presence of labeled test compound, added at a final concentration between about 10-300 nM. After incubation for 30-120 minutes, the cells are examined, e.g., by microscopy or FACS analysis, for intracellular label. The presence of significant intracellular label is evidence that the test compound is transported by facilitated or active transport.

In one embodiment of the invention, uptake into cells is enhanced by administering the antisense compound in combination with an arginine-rich peptide linked to the 5' or 3' end of the antisense oligomer. The peptide is typically 8-16 amino acids and consists of a mixture of arginine, and other amino acids including phenylalanine and cysteine, as discussed further below.

RNAse resistance. Two general mechanisms have been proposed to account for inhibition of expression by antisense oligonucleotides (Agrawal, Mayrand et al. 1990; Bonham, Brown et al. 1995; Boudvillain, Guerin et al. 1997). In the first, a heteroduplex formed between the oligonucleotide and the viral RNA acts as a substrate for RNaseH, leading to cleavage of the RNA. Oligonucleotides belonging, or proposed to belong, to this class include phosphorothioates, phosphotriesters, and phosphodiesters (unmodified "natural" oligonucleotides). Such compounds expose the RNA in an oligomer:RNA duplex structure to hydrolysis by RNaseH, and therefore loss of function.

A second class of oligonucleotide analogs, termed "steric blockers" or, alternatively, "RNaseH inactive" or "RNaseH resistant", have not been observed to act as a substrate for RNaseH, and act by sterically blocking target RNA nucleocytoplasmic transport, splicing, translation, or replication. This class includes methylphosphonates (Toulme, Tinevez et al. 1996), morpholino oligonucleotides, peptide nucleic acids (PNA's), certain 2'-O-allyl or 2'-O-alkyl modified oligonucleotides (Bonham, Brown et al. 1995), and N3'→P5' phosphoramidates (Ding, Grayaznov et al. 1996; Gee, Robbins et al. 1998).

A test oligomer can be assayed for its RNaseH resistance by forming an RNA:oligomer duplex with the test compound, then incubating the duplex with RNaseH under a standard assay conditions, as described (Stein, Foster et al. 1997). After exposure to RNaseH, the presence or absence of intact duplex can be monitored by gel electrophoresis or mass spectrometry.

In vivo uptake. In accordance with another aspect of the invention, there is provided a simple, rapid test for confirming that a given antisense oligomer type provides the required characteristics noted above, namely, high Tm, ability to be actively taken up by the host cells, and substantial resistance to RNaseH. This method is based on the discovery that a properly designed antisense compound will form a stable heteroduplex with the complementary portion of the RNA target when administered to a mammalian subject, and the heteroduplex subsequently appears in the urine (or other body fluid). Details of this method are also given in co-owned U.S. Pat. No. 6,365,351 for "Non-Invasive Method for Detecting Target RNA," the disclosure of which is incorporated herein by reference.

Briefly, a test oligomer containing a backbone to be evaluated, having a base sequence targeted against a known RNA, is injected into a mammalian subject. The antisense oligomer may be directed against any intracellular RNA, including RNA encoded by a host gene. Several hours (typically 8-72) after administration, the urine is assayed for the presence of the antisense-RNA heteroduplex. If heteroduplex is detected, the backbone is suitable for use in the antisense oligomers of the present invention.

The test oligomer may be labeled, e.g. by a fluorescent or a radioactive tag, to facilitate subsequent analyses, if it is appropriate for the mammalian subject. The assay can be in any suitable solid-phase or fluid format. Generally, a solid-phase assay involves first binding the heteroduplex analyte to a solid-phase support, e.g., particles or a polymer or test-strip substrate, and detecting the presence/amount of heteroduplex bound. In a fluid-phase assay, the analyte sample is typically pretreated to remove interfering sample components. If the oligomer is labeled, the presence of the heteroduplex is confirmed by detecting the label tags. For non-labeled compounds, the heteroduplex may be detected by immunoassay if in solid phase format or by mass spectroscopy or other known methods if in solution or suspension format.

Structural features. As detailed above, the antisense oligomer has a base sequence directed to a targeted portion of a cellular gene, preferably the region at or adjacent the start codon or a processed transcript or a region at or adjacent a splice site junction of the CD86 mRNA or preprocessed transcript. In addition, the oligomer is able to effectively inhibit expression of the targeted gene when administered to a host cell, e.g. in a mammalian subject. This requirement is met when the oligomer compound (a) has the ability to be taken up by dendritic cells and (b) once taken up, form a duplex with the target RNA with a Tm greater than about 45° C., preferably greater than 50° C.

The ability to be taken up selectively by activated immune cells requires, in part, that the oligomer backbone be substantially uncharged. The ability of the oligomer to form a stable duplex with the target RNA will depend on the oligomer backbone, the length and degree of complementarity of the antisense oligomer with respect to the target, the ratio of G:C to A:T base matches, and the positions of any mismatched bases. The ability of the antisense oligomer to resist cellular nucleases promotes survival and ultimate delivery of the agent to the cell cytoplasm.

Antisense oligonucleotides of 15-20 bases are generally long enough to have one complementary sequence in the mammalian genome. In addition, antisense compounds having a length of at least 12, typically at least 15 nucleotides in length hybridize well with their target mRNA. Due to their hydrophobicity, antisense oligonucleotides tend to interact well with phospholipid membranes, and it has been suggested that following the interaction with the cellular plasma membrane, oligonucleotides are actively transported into living cells (Loke, Stein et al. 1989; Yakubov, Deeva et al. 1989; Anderson, Xiong et al. 1999).

Oligomers as long as 40 bases may be suitable, where at least a minimum number of bases, e.g., 12 bases, are complementary to the target sequence. In general, however, facilitated or active uptake in cells is optimized at oligomer lengths less than about 30, preferably less than 25. For PMO oligomers, described further below, an optimum balance of binding stability and uptake generally occurs at lengths of 15-22 bases.

Morpholino oligonucleotides, particularly phosphoramidate- or phosphorodiamidate-linked morpholino oligonucleotides have been shown to have high binding affinities for complementary or near-complementary nucleic acids. Morpholino oligomers also exhibit little or no non-specific antisense activity, afford good water solubility, are immune to nucleases, and are designed to have low production costs (Summerton and Weller 1997).

The antisense activity of the oligomer may be enhanced by using a mixture of uncharged and cationic phosphorodiamidate linkages as shown in FIGS. 3G and 3H. The total number of cationic linkages in the oligomer can vary from 1 to 10, and be interspersed throughout the oligomer. Preferably the number of charged linkages is at least 2 and no more than half the total backbone linkages, e.g., between 2-8 positively charged linkages, and preferably each charged linkages is separated along the backbone by at least one, preferably at least two uncharged linkages. The antisense activity of various oligomers can be measured in vitro by fusing the oligomer target region to the 5' end a reporter gene (e.g. firefly luciferase) and then measuring the inhibition of translation of the fusion gene mRNA transcripts in cell free translation assays. The inhibitory properties of oligomers containing a mixture of uncharged and cationic linkages can be enhanced between, approximately, five to 100 fold in cell free translation assays.

Morpholino oligonucleotides (including antisense oligomers) are detailed, for example, in co-owned U.S. Pat. Nos. 5,698,685, 5,217,866, 5,142,047, 5,034,506, 5,166,315, 5,185,444, 5,521,063, and 5,506,337, all of which are expressly incorporated by reference herein In one preferred approach, antisense oligomers for use in practicing the invention are composed of morpholino subunits of the form shown in the above cited patents, where (i) the morpholino groups are linked together by uncharged linkages, one to three atoms long, joining the morpholino nitrogen of one subunit to the 5' exocyclic carbon of an adjacent subunit, and (ii) the base attached to the morpholino group is a purine or pyrimidine base-pairing moiety effective to bind, by base-specific hydrogen bonding, to a base in a polynucleotide. The purine or pyrimidine base-pairing moiety is typically adenine, cytosine, guanine, uracil or thymine. Preparation of such oligomers is described in detail in U.S. Pat. No. 5,185,444 (Summerton et al., 1993), which is hereby incorporated by reference in its entirety. As shown in this reference, several types of nonionic linkages may be used to construct a morpholino backbone.

Exemplary subunit structures for antisense oligonucleotides of the invention include the morpholino subunit types shown in FIGS. 1A-D, each linked by an uncharged, phosphorous-containing subunit linkage, as shown in FIGS. 2A-2D, respectively. In these figures, the X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures. Alkyl, alkoxy and thioalkoxy preferably include 1-6 carbon atoms, and more preferably 1-4 carbon atoms. Monosubstituted or disubstituted nitrogen preferably refers to lower alkyl substitution, and the cyclic structures are preferably 5- to 7-membered nitrogen heterocycles optionally containing 1-2 additional heteroatoms selected from oxygen, nitrogen, and sulfur. Z is sulfur or oxygen, and is preferably oxygen.

Figure 1B:
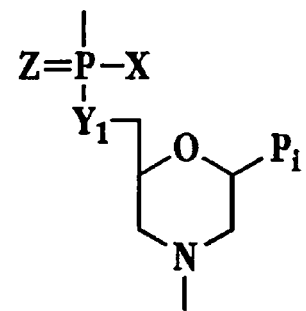
Figure 2A:
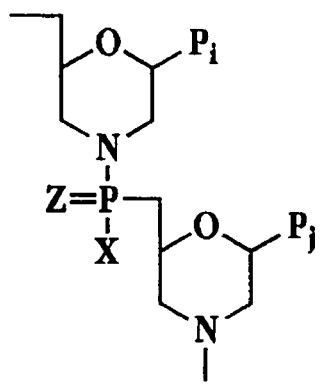
FIGS. 2A-2D show the repeating subunit segment of exemplary morpholino oligonucleotides, designated A through D, constructed using subunits A-D, respectively, of FIG. 1.
Figure 2B:
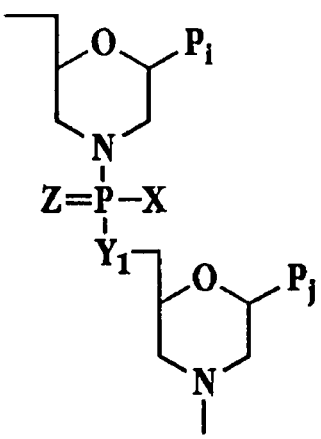
Figure 3A:
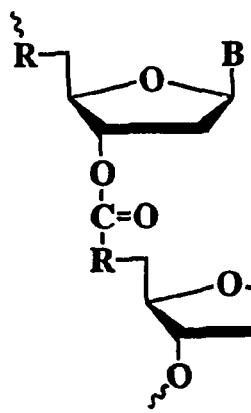
FIGS. 3A-3G show examples of uncharged linkage types in oligonucleotide analogs.
Figure 3B:
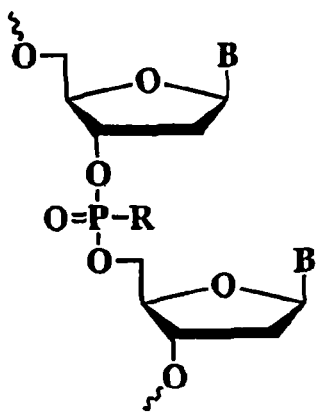
Figure 3C:
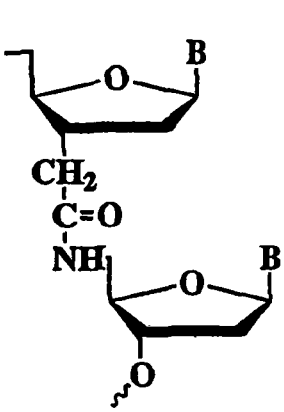
Figure 3D:
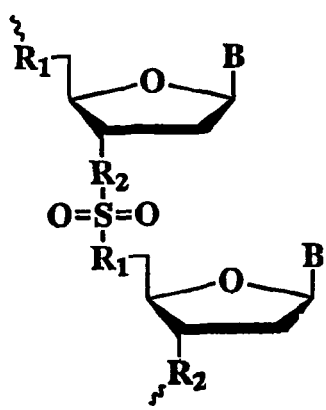
Figure 3E:
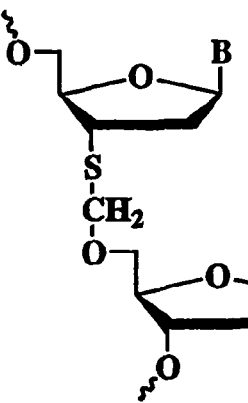
Figure 3F:
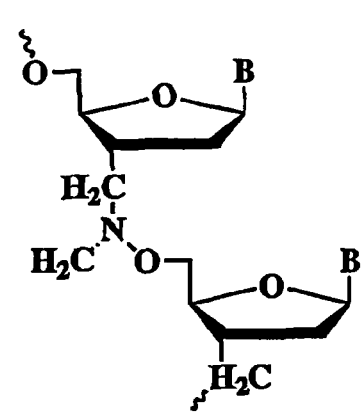
Figure 3G:
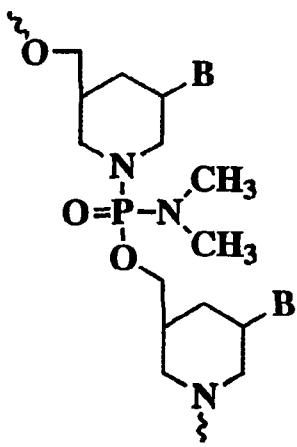
Figure 3H:
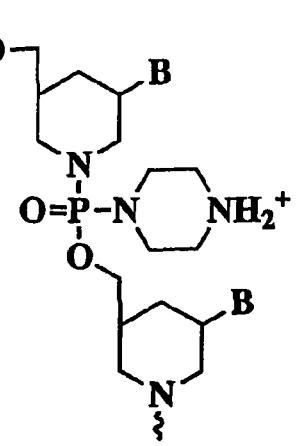
FIG. 3H is an example of a preferred charged, cationic linkage.

FIG. 1A shows a phosphorous-containing linkage which forms the five atom repeating-unit backbone shown in FIG. 2A, where the morpholino rings are linked by a 1-atom phosphoamide linkage. Subunit B in FIG. 1B is designed for 6-atom repeating-unit backbones, as shown in FIG. 2B. In FIG. 1B, the atom Y linking the 5' morpholino carbon to the phosphorous group may be sulfur, nitrogen, carbon or, preferably, oxygen. The X moiety pendant from the phosphorous may be any of the following: fluorine; an alkyl or substituted alkyl; an alkoxy or substituted alkoxy; a thioalkoxy or substituted thioalkoxy; or, an unsubstituted, monosubstituted, or disubstituted nitrogen, including cyclic structures. Z is sulfur or oxygen, and is preferably oxygen. Particularly preferred morpholino oligonucleotides include those composed of morpholino subunit structures of the form shown in FIG. 2B, where X is an amine or alkyl amine of the form $X=NR_2$, where R is independently H or $CH_3$, that is where $X=NH_2$, $X=NHCH_3$ or $X=N(CH_3)_2$, $Y=O$, and $Z=O$.

Figure 1C:
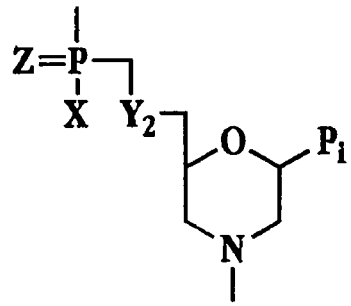
Figure 1D:
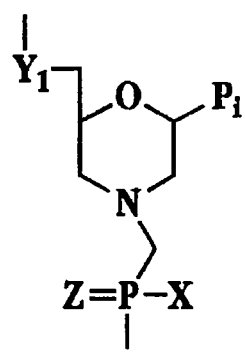
Figure 2C:
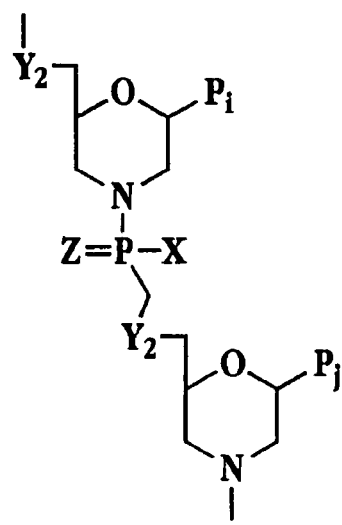
Figure 2D:
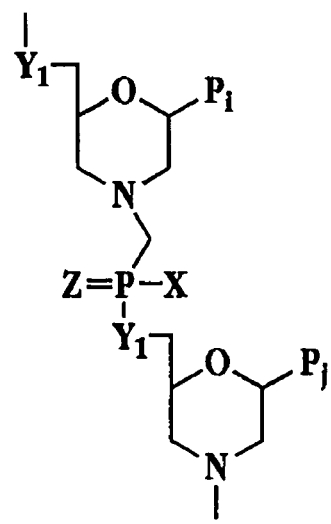

Subunits C-D in FIGS. 1C-D are designed for 7-atom unit-length backbones as shown for structures in FIGS. 2C and D. In Structure C, the X moiety is as in Structure B, and the moiety Y may be methylene, sulfur, or preferably oxygen. In Structure D, the X and Y moieties are as in Structure B. In all subunits depicted in FIGS. 1 and 2, each Pi and Pj is a purine or pyrimidine base-pairing moiety effective to bind, by base-specific hydrogen bonding, to a base in a polynucleotide, and is preferably selected from adenine, cytosine, guanine and uracil.

As noted above, the substantially uncharged oligomer may advantageously include a limited number of charged backbone linkages. One example of a cationic charged phophordiamidate linkage is shown in FIG. 3H. This linkage, in which the dimethylamino group shown in FIG. 3G is replaced by a 1-piperazino group as shown in FIG. 3G, can be substituted for any linkage(s) in the oligomer. By including between two to eight such cationic linkages, and more generally, at least two and no more than about half the total number of linkages, interspersed along the backbone of the otherwise uncharged oligomer, antisense activity can be enhanced without a significant loss of specificity. The charged linkages are preferably separated in the backbone by at least 1 and preferably 2 or more uncharged linkages.

More generally, the morpholino oligomers with uncharged backbones are shown in FIGS. 3A-3G. A substantially uncharged morpholino oligomer is illustrated by the phosphorodiamidate morpholino oligomer (PMO) shown in FIG. 3G. It will be appreciated that a substantially uncharged backbone may include one or more, e.g., up to 10-20% of charged intersubunit linkages, typically negatively charged phosphorous linkages. Also shown is a cationic linkage in FIG. 3H wherein the nitrogen pendant to the phosphate atom in the linkage of FIG. 3G is replaced with a 1-piperazino structure. The method for synthesizing the 1-piperazino group linkages is described below with respect to FIG. 10.

Antisense sequence. In the methods of the invention, the antisense oligomer is designed to hybridize to a region of the target nucleic acid sequence, under physiological conditions with a Tm substantially greater than 37° C., e.g., at least 45° C. and preferably 60° C.-80° C., wherein the target nucleic acid sequence is preferentially expressed in activated lymphocytes. The oligomer is designed to have high-binding affinity to the target nucleic acid sequence and may be 100% complementary thereto, or may include mismatches, e.g., to accommodate allelic variants, as long as the heteroduplex formed between the oligomer and the target nucleic acid sequence is sufficiently stable to withstand the action of cellular nucleases and other modes of degradation during its transit from cell to body fluid. Mismatches, if present, are less destabilizing toward the end regions of the hybrid duplex than in the middle. The number of mismatches allowed will depend on the length of the oligomer, the percentage of G:C base pair in the duplex and the position of the mismatch(es) in the duplex, according to well understood principles of duplex stability.

Although such an antisense oligomer is not necessarily 100% complementary to a nucleic acid sequence that is preferentially expressed in mature dendritic cells, it is effective to stably and specifically bind to the target sequence such that expression of the target sequence is modulated. The appropriate length of the oligomer to allow stable, effective binding combined with good specificity is about 8-40 nucleotide base units, and preferably about 12-25 nucleotides. Oligomer bases that allow degenerate base pairing with target bases are also contemplated, assuming base-pair specificity with the target is maintained.

mRNA transcribed from the relevant region of a gene associated with CD86 expression is generally targeted by the antisense oligonucleotides for use in practicing the invention, however, in some cases double-stranded DNA may be targeted using a non-ionic probe designed for sequence-specific binding to major-groove sites in duplex DNA. Such probe types are described in U.S. Pat. No. 5,166,315 (Summerton et al., 1992), which is hereby incorporated by reference, and are generally referred to herein as antisense oligomers, referring to their ability to block expression of target genes.

The antisense compound is targeted against an expression-sensitive region of a processed or preprocessed CD transcript, that is, a region which, when bound to the antisense compound, is effective to inhibit the expression of full-length CD86 in dendritic cells. In one general embodiment, the expression-sensitive region is one that includes or is adjacent the AUG start site of a processed transcript, where formation of an antisense-transcript heteroduplex is effective to inhibit translation of the transcript. Here the antisense compound has a base sequence that is complementary to a target region containing at least 12 contiguous bases in a processed human CD86 transcript, in the target region from about −20 to +30 bases with respect to the A nucleotide of the AUG start site at position 1, and which includes at least 6 contiguous bases of the sequence identified by SEQ ID NO: 9. Exemplary antisense sequences include those identified as SEQ ID NOS: 21-23, and 32.

In a more specific embodiment, the antisense compounds are designed to span or cover the three bases +12 to +14 bases (where the A nucleotide of the AUG start site represents +1). In this embodiment, the antisense compound may hybridize to a region spanning these bases, e.g., where the three bases are in the middle of the target region, or may hybridize to a region predominantly upstream of and including these bases, e.g., the target bases extending from −2 to +19 (SEQ ID NO: 23 below), or may hybridize to a region predominantly downstream of and including these bases, e.g., the target bases extending from +9 to +30 (SEQ ID NO: 32 below).

In another general embodiment, the expression-sensitive region is a splice-site target region that may include (i) an intron region adjacent, e.g., within 5 bases of, a splice-site donor or acceptor junction, (ii) a region spanning a donor or acceptor splice-site junction, or (iii) the exon region adjacent, e.g., within 5 bases of, a splice-site donor or acceptor junction. The target region preferably contains at least 12 contiguous bases in a preprocessed human CD86 transcript, and includes, in exemplary embodiment, at least 6 contiguous bases of one of the sequences identified by SEQ ID NOS: 10-14. Exemplary antisense sequences include those identified as SEQ ID NOS: 24-28.

However, in some cases, other regions of the CD86 mRNA (SEQ ID NO: 29) may be targeted, including one or more of, an initiator or promoter site, a 3'-untranslated region, and a 5'-untranslated region. Both spliced and unspliced, preprocessed RNA may serve as the template for design of antisense oligomers for use in the methods of the invention.

When the antisense compound is complementary to a specific region of a target gene (such as the region adjacent the AUG start codon of the CD86 gene) the method can be used to monitor the binding of the oligomer to the CD86 RNA.

The antisense compounds for use in practicing the invention can be synthesized by stepwise solid-phase synthesis, employing methods detailed in the references cited above. The sequence of subunit additions will be determined by the selected base sequence. In some cases, it may be desirable to add additional chemical moieties to the oligomer compounds, e.g. to enhance the pharmacokinetics of the compound or to facilitate capture or detection of the compound. Such a moiety may be covalently attached, typically to the 5'- or 3'-end of the oligomer, according to standard synthesis methods. For example, addition of a polyethyleneglycol moiety or other hydrophilic polymer, e.g., one having 10-100 polymer subunits, may be useful in enhancing solubility. One or more charged groups, e.g., anionic charged groups such as an organic acid, may enhance cell uptake. A reporter moiety, such as fluorescein or a radiolabeled group, may be attached for purposes of detection.

Alternatively, the reporter label attached to the oligomer may be a ligand, such as an antigen or biotin, capable of binding a labeled antibody or streptavidin. In selecting a moiety for attachment or modification of an oligomer antisense, it is generally of course desirable to select chemical compounds of groups that are biocompatible and likely to be tolerated by cells in vitro or in vivo without undesirable side effects.

B. Arginine-Rich Polypeptide Moiety

The use of arginine-rich peptide sequences conjugated to uncharged antisense compounds, e.g., PMO, has been shown to enhance cellular uptake in a variety of cells (Wender, Mitchell et al. 2000; Moulton, Hase et al. 2003; Moulton and Moulton 2003) (Iversen, Moulton et al. U.S. Patent Application No. 60/466,703, now U.S. publication No. 2004/0265879 A1, published Dec. 30, 2004, all of which are incorporated herein by reference.

In one embodiment of the invention, the antisense compound is covalently linked at its 3' or 5' end to an arginine rich-peptide effective to enhance uptake of the compound into dendritic cells relative to uptake in the absence of the peptide. The arginine-rich peptide is detailed in the above references to Moulton et al., and described in U.S. patent application. Preferably, the peptide is composed of d-amino acids, l-amino acids, non-natural amino acids or a combination thereof. Exemplary arginine-rich peptides include those identified by SEQ ID NOS: 1-3, of which those identified as SEQ ID NOS: 1 and 2 are preferred.

The transport peptide may significantly enhance cell entry of attached uncharged oligomer compounds, relative to uptake of the compound in the absence of the attached transport moiety, and relative to uptake by an attached transport moiety lacking the hydrophobic subunits Y. Such enhanced uptake is preferably evidenced by at least a two-fold increase, and preferably a four-fold increase, in the uptake of the compound into mammalian cells relative to uptake of the agent by an attached transport moiety lacking the hydrophobic subunits Y. Uptake is preferably enhanced at least twenty fold, and more preferably forty fold, relative to the unconjugated compound.

A further benefit of the transport moiety is its expected ability to stabilize a duplex between an antisense oligomer and its target nucleic acid sequence, presumably by virtue of electrostatic interaction between the positively charged transport moiety and the negatively charged nucleic acid. The number of charged subunits in the transporter is less than 14, as noted above, and preferably between 8 and 11, since too high a number of charged subunits may lead to a reduction in sequence specificity.

The transport moiety may also lower the effective concentration of an antisense oligomer to achieve antisense activity as measured in both tissue culture and cell-free systems. Cell-free translation systems provide an independent means to assess the enhanced effect of the transport moiety on the antisense oligomer's ability to bind to its target and, through steric blocking, inhibit translation of downstream sequences.

C. rTAT (P002) Peptide

In studies conducted in support of the present invention, several different "arginine-rich" peptide sequences were conjugated to fluorescent tagged PMO (PMO-fl) and examined to determine the effect of peptide sequence on uptake into lymphocytes. Enhanced uptake was observed for all arginine-rich peptide-PMO conjugates tested compared to unconjugated PMO. The P003 and P005 arginine-rich peptides (SEQ ID NOS: 2 and 3, respectively) provide enhanced uptake into lymphocytes regardless of the cell activation state. However, among the arginine-rich peptides examined, the rTAT (P002) peptide [NH$_2$-RRRQRRKKRC-COOH] (SEQ ID NO: 1) PMO conjugate exhibited differential uptake into dendritic cells dependent on cell activation status. PMO uptake was greatly increased in mature dendritic cells as shown below as well as activated B cells and CD4 and CD8 T cells when compared to naïve lymphocytes (Mourich, Moulton et al. U.S. Patent Application No. 60/505,418). Furthermore, experiments in support of the invention demonstrate that the arginine-rich peptide-antisense compounds conjugates alone do not affect the maturation state of dendritic cells. This was shown by treating dendritic cells with arginine-rich peptide-PMO conjugates in the absence of a maturation stimulus and observing no activation of the dendritic cell population.

The rTAT peptide can be synthesized by a variety of known methods, including solid-phase synthesis. The amino acid subunits used in construction of the polypeptide may be either l- or d-amino acids, preferably all l-amino acids or all d-amino acids. Minor (or neutral) amino acid substitutions are allowed, as long as these do not substantially degrade the ability of the polypeptide to enhance uptake of antisense compounds selectively into activated T cells. One skilled in the art can readily determine the effect of amino acid substitutions by construction of a series of substituted rTAT polypeptides, e.g., with a given amino acid substitution separately at each of the positions along the rTAT chain. Using the above test for uptake of fluoresceinated PMO-polypeptide conjugate, one can then determine which substitutions are neutral and which significantly degrade the transporter activity of the peptide. Rules for neutral amino acid substitutions, based on common charge and hydrophobicity similarities among distinct classes of amino acids are well known and applicable here. In addition, it will be recognized that the C-terminal cysteine of SEQ ID NO: 1 is added for purposes of coupling to the antisense compound, and may be replaced/deleted when another terminal amino acid or linker is used for coupling.

The rTAT polypeptide can be linked to the compound to be delivered by a variety of methods available to one of skill in the art. The linkage point can be at various locations along the transporter. In selected embodiments, it is at a terminus of the transporter, e.g., the C-terminal or N-terminal amino acid. In one exemplary approach, the polypeptide has, as its C-terminal residue, a single cysteine residue whose side chain thiol is used for linking. Multiple transporters can be attached to a single compound if desired.

When the compound is a PMO, the transporter can be attached at the 5' end of the PMO, e.g. via the 5'-hydroxyl group, or via an amine capping moiety, as described (Moulton and Moulton 2003) (Iversen, Moulton et al. U.S. Patent Application No. 60/466,703). Alternatively, the transporter may be attached at the 3' end, e.g. via a morpholino ring nitrogen, as described (Moulton and Moulton 2003) (Iversen, Moulton et al. U.S. Patent Application No. 60/466,703), either at a terminus or an internal linkage. The linker may also comprise a direct bond between the carboxy terminus of a transporter peptide and an amine or hydroxy group of the PMO, formed by condensation promoted by, for example carbodiimide.

Linkers can be selected from those which are non-cleavable under normal conditions of use, e.g., containing a thioether or carbamate bond. In some embodiments, it may be desirable to include a linkage between the transporter moiety and compound which is cleavable in vivo. Bonds which are cleavable in vivo are known in the art and include, for example, carboxylic acid esters, which are hydrolyzed enzymatically, and disulfides, which are cleaved in the presence of glutathione. It may also be feasible to cleave a photolytically cleavable linkage, such as an ortho-nitrophenyl ether, in vivo by application of radiation of the appropriate wavelength.

For example, the preparation of a conjugate having a disulfide linker, using the reagent N-succinimidyl 3-(2-pyridyldithio) propionate (SPDP) or succinimidyloxycarbonyl α-methyl-α-(2-pyridyldithio) toluene (SMPT), is described (Moulton and Moulton 2003) (Iversen, Moulton et al. U.S. Patent Application No. 60/466,703). Exemplary heterobifunctional linking agents which further contain a cleavable disulfide group include N-hydroxysuccinimidyl 3-[(4-azidophenyl)dithio]propionate and others.

IV. Selective Uptake of rTat-Antisense Oligomers into Activated Dendritic Cells

The present invention provides a method and composition for delivering therapeutic compounds, e.g., uncharged antisense compounds, specifically to activated immune cells, e.g., antigen-activated T cells, B cells, and mature dendritic cells.

Figure 5:
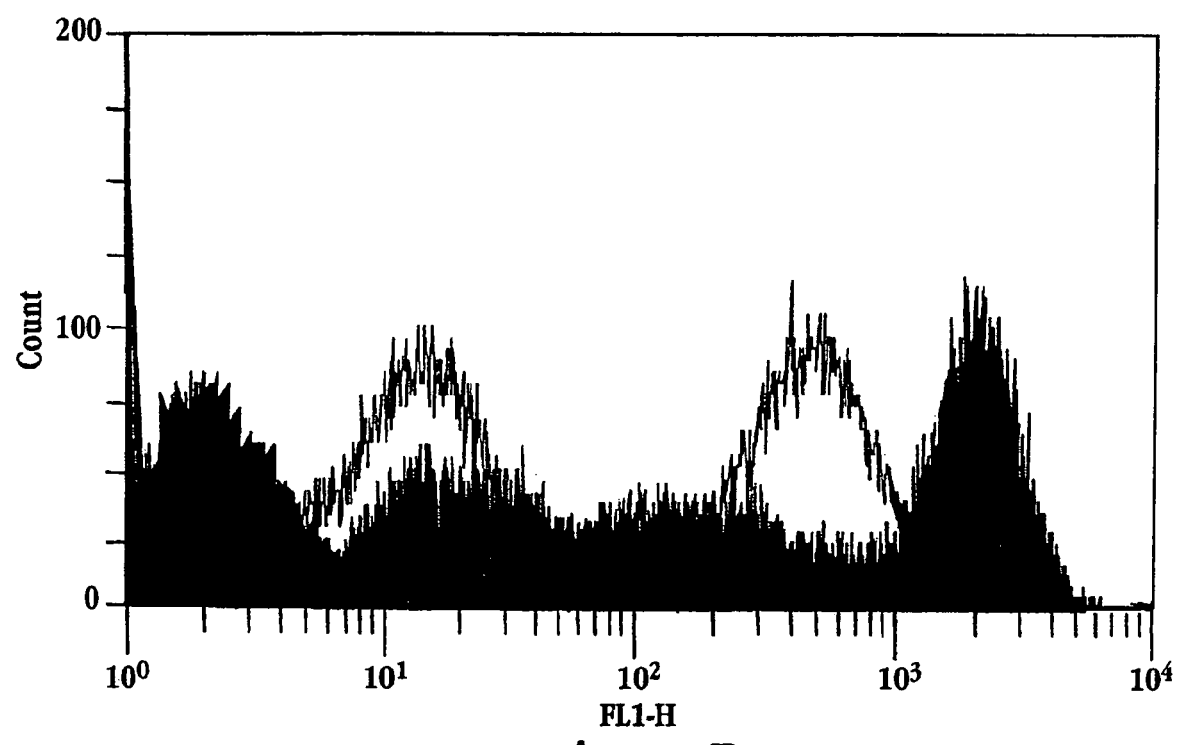
FIG. 5 shows a fluorescence activated cell sorting (FACS) analysis of the uptake of fluorescein-labeled peptide-PMO conjugates into dendritic cells subjected to lipopolysaccharide (LPS) activation.

The ability of the rTat (SEQ ID NO:1, P002) peptide to enhance uptake of a fluoresceinated PMO antisense compound selectively into activated mouse dendritic cells is demonstrated in the study described in Example 1, and with the results shown in FIG. 5. In this study, cultured mouse dendritic cells were incubated with fluorescein-labeled P002-PMO conjugate and subjected to lymphocyte activating substances, as described in Example 1. Dendritic cells were stained with antibody to determine the extent of uptake by FACS analysis of the cells. The results show relatively low uptake of the antisense PMO into non-activated dendritic cells. Activation by lipopolysaccharide (LPS) caused significantly increased uptake of the antisense oligomer into dendritic cells.

The property of activation-dependent uptake of peptide-antisense conjugate is not observed with other arginine-rich peptides, which are known to enhance drug transport into cells. This is also demonstrated by the study described in Example 1, and with the results shown in FIG. 5. As seen in these figures, P003-PMO conjugate (corresponding to the arginine-rich peptide of SEQ ID NO: 2) is readily taken up by immature dendritic cells. PMO alone is relatively poorly taken up by immature dendritic cells, and P002-PMO shows enhanced uptake into LPS treated dendritic cells.

In one aspect of the invention, therefore, the P002 peptide may be conjugated to a substantially uncharged antisense compound, to enhance its uptake selectively into antigen-activated, mature dendritic cells, including antigen-activated, mature human dendritic cells.

V. Treating Transplantation Rejection and Autoimmune Disorder

By manipulating the immune system's normal mechanism for the generation of immune tolerance to self antigens, the present invention provides a method and composition that alters the function and activity of mature dendritic cells in a way that is advantageous in the treatment of transplantation rejection or autoimmune disorders, such as multiple sclerosis, lupis, myathenia gravis, inflammatory bowel disease and rheumatoid arthritis.

By employing an antisense compound against CD86 (e.g., SEQ ID NOS: 21-28 and 32), the present invention provides a means to precisely and specifically block T cell activation to an antigen presented by a mature dendritic cell. This allows the generation of a tolerized T cell and dendritic cell population responding to transplanted tissue, when chronically activated as in an autoimmune condition, or by an immunogenic therapeutic protein. Where the antisense compound is linked to an rTAT peptide, the conjugate preferentially targets activated dendritic cells, thus allowing the therapy to be made highly specific for mature dendritic cells.

The generation of tolerized, anergic T-cells using the compounds and methods of the invention also provides a long-lasting tolerance that has a variety of therapeutic advantages.

A. CD86 Antisense Oligomers, T Cell Costimulation and IL10 Production by Mature Dendritic Cells.

Dendritic cells (DCs) reside and traffic through most tissues of the body in an immature state. Upon encountering an inflammatory stimulus changes in DC phenotype rapidly ensue. Hallmarks of this phenotypic shift termed "maturation" include the loss of phagocytic function, increased surface expression of MHC class I, II, adhesion molecules, distinct chemokine receptors and costimulatory molecules such as B7-1 (CD80) and B7-2 (CD86). Together these provide mature DCs the ability to traffic to lymphoid tissue and the capacity to be potent antigen presenting cells (APCs) to naïve T cells. The cascade of signaling events that follow when CD28 on the responding T cell is engaged by CD86 are well established. However, little is known about the reciprocity of events occurring in APCs due to the expression or engagement of CD80 and CD86 molecules. Studies to determine if antisense molecules could enter DCs and be used to inhibit the expression of CD86 molecules led unexpectedly to the observations described in the present invention that APCs, specifically dendritic cells, undergo important alterations when B7 molecules are engaged. These observations include a link between the expression of CD86 and the regulation of IL-10 expression in bone marrow-derived mature DCs.

Exemplary target sequences for the CD86 (B7-2) gene are listed in Table 1 below. The murine CD86 sequences are noted with "mu" and are derived from Genbank Accession No. AF065898. The human CD86 AUG target and targeting sequences are noted with "hu" and derived from Genbank Accession No. NM006889. The human Exon 6, 7, and 8 splice donor (sd) and splice acceptor (sa) target and targeting sequences are derived from Genbank Accession Nos. U17720, U17721 and U17722, respectively.

TABLE 1

Exemplary CD86 Target Sequences

| Oligomer Target | Sequence (5' to 3') | Sp. | Nct. Range | SEQ ID NO. |
| --- | --- | --- | --- | --- |
| CD86 AUG | cggaagcacccacgatggacccccag | mu | 19-43 | 4 |
| Exon 7sa | gctgtttccgtggagacgc | mu | 99-117 | 5 |
| Exon 9sd | gccgaatcagcttagcagg | mu | 833-851 | 6 |

TABLE 1-continued

Exemplary CD86 Target Sequences

| Oligomer Target | Sequence (5' to 3') | Sp. | Nct. Range | SEQ ID NO. |
|---|---|---|---|---|
| Exon 10sa | gcccagcaacacagcctct | mu | 851-869 | 7 |
| Exon 11sa | gaaaccaaatgcagagtg | mu | 944-961 | 8 |
| CD86 AUG | catttgtgacagcactatgggactgag<u>taa</u>cattct ctttgtgatg | hu | 132-177 | 9 |
| CD86Ex6sa | agcttgaggaccctcagcctc | hu | 170-190 | 10 |
| CD86Ex6sd | gcctcgcaactcttataaatgtg | hu | 291-313 | 11 |
| CD86Ex7sa | gaaccaacacaatggagaggga | hu | 274-295 | 12 |
| CD86Ex7sd | gagtgaacagaccaagaaaag | hu | 298-319 | 13 |
| CD86Ex8sa | agaaaaaatccatatacctgaa | hu | 223-244 | 14 |

TABLE 2

Exemplary CD86 Targeting Sequences

| Oligomer Target | Sequence (5' to 3') | Sp. | SEQ ID NO. |
|---|---|---|---|
| B7-2 AUG1 | CTGGGGTCCATCGTGGGTGC | mu | 15 |
| B7-2 AUG2 | GGGGTCCATCGTGGGTGCTTCCG | mu | 16 |
| Exon 7sa | GCGTCTCCACGGAAACAGC | mu | 17 |
| Exon 9sd | CCTGCTAAGCTGATTCGGC | mu | 18 |
| Exon 10sa | AGAGGCTGTGTTGCTGGGC | mu | 19 |
| Exon 11sa | CACTCTGCATTTGGTTTC | mu | 20 |
| CD86 AUG1 | GTTACTCAGTCCCATAGTGCTG | hu | 21 |
| CD86 AUG2 | CCATAGTGCTGTCACAAATG | hu | 22 |
| CD86 AUG3 | GAATGTTACTCAGTCCCATAG | hu | 23 |
| CD86Ex6sa | GAGGCTGAGGGTCCTCAAGCT | hu | 24 |
| CD86Ex6sd | CACATTTATAAGAGTTGCGAGGC | hu | 25 |
| CD86Ex7sa | TCCCTCTCCATTGTGTTGGTTC | hu | 26 |
| CD86Ex7sd | CTTTTCTTGGTCTGTTCACTC | hu | 27 |
| CD86Ex8sa | TTCAGGTATATGGATTTTTCT | hu | 28 |
| CD86 AUG4 | CATCACAAAGAGAATGTTACTC | hu | 32 |

B. Treatment Methods

In one aspect, the invention is directed to methods of inducing immunological tolerance in vivo in a patient, by administering to the patient a therapeutically effective amount of a peptide-conjugated CD86 PMO pharmaceutical composition, as described herein, e.g., a pharmaceutical composition comprising an antisense oligomer to CD86.

The antisense oligomers of the invention can be effective in the treatment of patients by modulating the immunological response to allogeneic transplantation or elimination of chronically activated T cells in the case of autoimmune diseases.

In one embodiment, a subject is in need of tolerized dendritic cells and T cells when responding to an allogeneic transplantation. In this embodiment, a CD86 antisense compound is administered to the subject in a manner effective to result in blocking the formation of activated T cells. Typically, the patient is treated with the conjugate shortly before, e.g., a few days before, receiving the transplant, then treated periodically, e.g., once every 14 days, until immunological tolerance is established. Immunological tolerance can be monitored during treatment by testing patient T cells for reactivity with donor MHC antigens in a standard in vitro test, as detailed below.

For the treatment of an autoimmune disorder, such as multiple sclerosis, lupis, myathenia gravis, inflammatory bowel disease and rheumatoid arthritis, the patient is given an initial single dose of the CD86 antisense conjugate, then additional doses on a periodic basis, e.g., every 3-14 days, until improvement in the disorder is observed. As above, development of immunological tolerance can be monitored during treatment by testing T cells from a blood sample for their ability to react with a selected, relevant antigen in vitro.

It will be understood that in vivo administration of such a CD86 antisense compound is dependent upon, (1) the duration, dose and frequency of antisense administration, and (2) the general condition of the subject. A suitable dose can be approximated from animal model studies and extrapolated to patient weight.

Typically, one or more doses of CD86 antisense oligomer are administered, generally at regular intervals for a period of about one to two weeks. Preferred doses for oral administration are from about 1 mg oligomer/patient to about 25 mg oligomer/patient (based on an adult weight of 70 kg). In some cases, doses of greater than 25 mg oligomer/patient may be necessary. For IV administration, the preferred doses are from about 1.0 mg oligomer/patient to about 100 mg oligomer/patient, preferably 5-50 mg oligomer/patient, (based on an adult weight of 70 kg). The antisense agent is generally administered in an amount sufficient to result in a peak blood concentration of at least 200-400 nM antisense oligomer.

In general, the method comprises administering to a subject, in a suitable pharmaceutical carrier, an amount of a CD86 antisense oligomer, e.g., morpholino oligomer, effective to inhibit expression of CD86 and increase expression of IL-10 in dendritic cells.

Effective delivery of an antisense oligomer to the target nucleic acid is an important aspect of the methods described herein. In accordance with the invention, such routes of antisense oligomer delivery include, but are not limited to, inhalation; transdermal delivery; various systemic routes, including oral and parenteral routes, e.g., intravenous, subcutaneous, intraperitoneal, or intramuscular delivery.

It is appreciated that any methods which are effective to deliver a CD86 PMO to the cells of an allogeneic transplant or to introduce the agent into the bloodstream are also contemplated.

In preferred applications of the method, the subject is a human subject and the methods of the invention are applicable to treatment of any condition wherein promoting immunological tolerance would be effective to result in an improved therapeutic outcome for the subject under treatment.

It will be understood that an effective in vivo treatment regimen using a CD86 antisense compound in the methods of the invention will vary according to the frequency and route of administration as well as the condition of the subject under treatment. Accordingly, such in vivo therapy will generally require monitoring by tests appropriate to the condition being treated and a corresponding adjustment in the dose or treatment regimen in order to achieve an optimal therapeutic outcome.

C. Ex Vivo Treatment of Human Dendritic Cells

In another preferred application of the method, autologous dendritic cells isolated from a human subject can be treated ex vivo with the CD86 antisense compound in the presence of a selected, relevant antigen. Studies in several systems have demonstrated that when dendritic cells are pulsed with antigens ex vivo, and these cells are subsequently readministered to the human subject from whom they were isolated, specific immunity can be established (Lu, Arraes et al. 2004; Mohamadzadeh and Luftig 2004). A similar strategy can be used to establish, ex vivo, a tolerogenic population of dendritic cells using the methods and compositions of the present invention. Dendritic cells are isolated from the peripheral blood of a human subject using methods well-known to those skilled in the art. Growth and treatment of the dendritic cells with the relevant antigen and antisense CD86 antisense will induce the formation of dendritic cells that, upon readministration to the subject, will condition the dendritic cells to induce a T-cell response that suppresses the antigen-specific immunity. This application of the method is particularly useful in treating an autoimmune disorder where the immune system is reacting inappropriately to specific antigens and these antigens can be used to condition the dendritic cells. An example is the immune-mediated destruction of myelin in multiple sclerosis (MS). Myelin basic protein (MBP) and proteolipid protein (PLP) are host proteins which are thought to be the key antigens in the etiology of this autoimmune disease (Shevac 2002).

D. Administration of Anti-CD86 Antisense Oligomers

Transdermal delivery of an antisense oligomer may be accomplished by use of a pharmaceutically acceptable carrier. One example of morpholino oligomer delivery is described in PCT patent application WO 97/40854, incorporated herein by reference.

In one preferred embodiment, the oligomer is an anti-CD86 morpholino oligomer, contained in a pharmaceutically acceptable carrier, and delivered orally. In a further aspect of this embodiment, the antisense oligomer is administered at regular intervals for a short time period, e.g., daily for two weeks or less. However, in some cases the antisense oligomer is administered intermittently over a longer period of time.

It follows that a morpholino antisense oligonucleotide composition may be administered in any convenient vehicle, which is physiologically acceptable. Such an oligonucleotide composition may include any of a variety of standard pharmaceutically accepted carriers employed by those of ordinary skill in the art. Examples of such pharmaceutical carriers include, but are not limited to, saline, phosphate buffered saline (PBS), water, aqueous ethanol, emulsions such as oil/water emulsions, triglyceride emulsions, wetting agents, tablets and capsules. It will be understood that the choice of suitable physiologically acceptable carrier will vary dependent upon the chosen mode of administration.

In some instances liposomes may be employed to facilitate uptake of an antisense oligonucleotide into cells. (See, e.g., Williams, 1996; Lappalainen, et al., 1994; Uhlmann, et al., 1990; Gregoriadis, 1979.) Hydrogels may also be used as vehicles for antisense oligomer administration, for example, as described in WO 93/01286. Alternatively, an oligonucleotide may be administered in microspheres or microparticles. (See, e.g., Wu et al., 1987).

Sustained release compositions are also contemplated within the scope of this application. These may include semipermeable polymeric matrices in the form of shaped articles such as films or microcapsules.

E. Monitoring Treatment

The efficacy of a given therapeutic regimen involving the methods described herein, may be monitored, e.g., by conventional FACS assays for the phenotype of cells in the circulation of the subject under treatment or cells in culture. Such analysis is useful to monitor changes in the numbers of cells of various lineages, in particular, activated T and B cells in response to an allogeneic transplant.

Phenotypic analysis is generally carried out using monoclonal antibodies specific to the cell type being analyzed. The use of monoclonal antibodies in such phenotypic analyses is routinely employed by those of skill in the art for cellular analyses and monoclonal antibodies specific to particular cell types are commercially available.

The CD86 PMO treatment regimen may be adjusted (dose, frequency, route, etc.), as indicated, based on the results of the phenotypic and biological assays described above.

From the foregoing, it will be appreciated how various objects and features of the invention are met. The specific blockade of dendritic cell activation of T cells capable of rejecting transplanted tissues is an important therapy for numerous human diseases where immunological tolerance is beneficial. The present invention provides a method of specifically blocking the activation of these cells through the use of antisense oligomers designed to inhibit CD86 expression, or specific portions of CD86, during the stage of antigen-specific activation and the generation of anergic, tolerized T cells. Antisense CD86 mediated suppression of either chronically activated T cells (i.e. autoimmunity) or naïve T cell responding to alloantigens (transplantation) provides a potent and specific therapeutic effect.

Additionally, this treatment method is long lived because the immune system is unable to replenish antigen-specific T cell clones once the precursor population is removed from the T cell repertoire. In addition, by specifically targeting the antisense CD86 oligomer to mature dendritic cells, immature dendritic cells would be unaffected, allowing for the patient to respond normally to foreign antigens as soon as the therapy is withdrawn. Moreover, the immune status of the patient prior to the antisense CD86 therapy (e.g. immunity provided by previous vaccinations or infections) would remain intact.

The following examples illustrate but are not intended in any way to limit the invention.

Materials and Methods

A. Antisense Oligomers and Peptide Conjugates

PMO synthesis, peptide conjugation and purification were preformed at AVI BioPharma Inc. (Corvallis, Oreg.) as previously described (Summerton and Weller 1997). Oligomer sequences were designed to either block translation by binding to bases surrounding the AUG start site (CAT) or alter RNA splicing by blocking splice donor or splice acceptor sites, sa or sd, respectively. An oligomer with the same base composition of the B7-2 (AUG) in a scrambled order was synthesized to serve as a control for oligomer treatment. B7-1 and B7-2 antisense oligomer sequences were designed using Genbank sequences accession numbers X60958 and U39459-66, respectively, The PMO sequences and designations are as follows; B7-1 (AUG) 5'-GCA AGC CAT AGC TTC AGA TGC-3' (SEQ ID NO:29), B7-2(AUG) 5'-CT GGG GTC CAT CGT GGG TGC-3'(SEQ ID NO:15), EXON 7sa 5'-GCG TCT CCA CGG AAA CAG C-3' (SEQ ID NO:17), EXON 9sd 5'-CCT GCT MG CTG ATT CGG C-3' (SEQ ID NO:18), EXON 10sa 5'-AGA GGC TGT GTT GCT GGG C-3' (SEQ ID NO:19), EXON 11sa 5'-CAC TCT GCA TTT GGT TTC-3' (SEQ ID NO:20), SCRAMBLE 5'-CGT GGT GCA CTG CGT GTG GC-3' (SEQ ID NO:30), 705-FL 5'-CCT CTT ACC TCA GTT ACA-FL-3' (SEQ ID NO:31). The 3' fluorescein conjugated oligomer 705-FL targets an irrelevant gene (human b-globin intron 2) and was used to analyze the intracellular delivery properties of different peptides into cultured DCs. Three different arginine rich peptide sequences were conjugated separately to the PMOs used in this study; P002=N-RRRQRRKKRGYC-CONH$_2$ (SEQ ID NO:1), P003=N-RRRRRRRRRFFC-CONH$_2$ (SEQ ID NO:2) and P005=N-RRRQRRKKRGYFFC-CONH$_2$ (SEQ ID NO:3).

B. Generation and Culturing of Bone Marrow Derived DCs

Murine DCs were generated by culturing marrow flushed from the femur and tibia of female BALB/c mice obtained from Jackson Laboratory aged 6-12 weeks. The marrow was minced through a 70 micron nylon cell strainer (BD Falcon) and washed twice after centrifugation in DMEM+1% fetal bovine serum (FBS) and penicillin streptomycin and glutamine (PSG). Cell suspension were made in culture medium (RPMI+10% FBS, PSG and $5\times10^{-5}$ M 2-mecapotoethanol) supplemented with recombinant mouse GM-CSF (eBioscience) [25 ng/ml] and seeded onto a 100 mm bacteriological Petri dish (Falcon) at $2\times10^5$ cells/ml. After 3 days an additional 5 ml of fresh medium was added containing GM-CSF. The culture supernatant was removed on the 6$^{th}$ day and centrifuged to recover any dislodged cells. The cell pellet was suspended in 10 ml fresh media with GM-CSF, placed back on to the original 100 mm dish and cultured for an additional 2-4 days prior to treatment with PMO.

Non-adherent cells were harvested by gentle pipetting of the medium which was then transferred to a tube for centrifugation at room temperature. The cell pellet was washed twice and then enumerated. The wells of a 12 well plate were seeded with 1.5 ml [$5\times10^5$ cells/ml] in fresh culture medium containing GM-CSF. PMO working stock [1 mM] in sterile water was added directly to the wells to obtain a final concentration ranging from 2-20 µM 2-4 hours prior to inducing maturation. Control culture wells were treated with the equivalent amount of sterile water. Maturation was induced by the addition of lipopolysaccharide (LPS) *E. coli* 026:B6 (Sigma) [1 µg/ml] or anti-CD40 (eBioscience) at [5 µg/ml] for 16 hours following PMO treatment. Culture conditions to block binding of cell associated ligand to B7 molecules was carried out by addition of [5 µg/ml] recombinant chimeric CTLA-4 FC non-cytolytic molecule (Chimerigen Allston, Mass.). Cultures used for analysis of IL-4 and IL-12 cytokine production were treated with 1 µl of the protein transport inhibitor brefeldin A GolgiPlug (BD Pharmingen) for the last 4 hrs of incubation.

C. Flow Cytometric Analysis

Cells were removed from culture wells by scrapping with a 25 cm cell scraper (Sarstedt) and rinsing with 1 ml cold FACS buffer [PBS+2% FBS+0.2% sodium azide]. The cells were washed twice in cold FACS buffer after centrifugation and suspended in 50 ml FACS buffer containing 1 µg anti-mouse CD16/CD32 FC blocking antibody (eBioscience) for 15 min on ice. The FC blocked samples were centrifuged and suspended in 50 ml antibody staining reagent for 30 min on ice. The surface staining reagents used were; CD11c-APC (BD Bioscience) and CD86-PE, CD86-FITC and CD80-PE (eBioscience) diluted in 50 ml cold FACS buffer. Stains were combined in the 50 ml when dual surface staining was needed for analysis. Cells were washed thrice by centrifugation in FACS buffer prior to analysis or use in additional staining procedures.

Intracellular cytokine staining was performed immediately following surface staining and washes. The cells were fixed and permeabilized in 100 µl Cytofix/Cytoperm (Pharmingen) buffer for 20 min on ice. Cell pellets were suspended in 50 µl of 1× Perm/Wash buffer (Pharmingen) containing either IL-10-FITC or IL-12-APC and IL-4-FITC (Pharmingen) and incubated for 30 min on ice. The cells were washed thrice and suspended in 300 ml FACS buffer prior collection of flow cytometric data on a FACS caliber cytometer (Becton Dickinson). Cytometric data was analyzed using FCS Express Software (Denovo Software).

D. RT-PCR

After treatment with PMO conjugates for 4 hours and then for 16 hours with LPS [1.0 µg/ml] total cellular RNA was isolated from the cultured cells using RNAeasy Mini kit (Qiagen) according to manufacture's instructions. The isolated RNA was treated with RNAse free DNAse I (2 U) for 30 min at 37° C. to eliminate contaminating genomic DNA followed by heating to 70° C. for 20 min to inactivation the enzyme. This material was used as template for single-tube reverse transcription and polymerase chain reaction using SuperScript One-Step RT-PCR with Platinum Taq enzyme (Invitrogen). Primers spanning 870 bp of the B7-2 mRNA, forward primer 5'-GGCAATCCTTATCTTTGTGACAGTC-3' (SEQ ID NO: 34) and reverse primer: 5'-TTTGCTGAAG-CAATTTGGGG-3' (SEQ ID NO: 35) were used to examine splice altering activity of the PMOs. Primers to detect mouse IL-10 mRNA forward primer 5'-GATCCAGGGATCT-TAGCTAACGG-3' (SEQ ID NO: 36) and reverse primer 5'-TTCTCTTCCCAAGACCCATGAGT-3' (SEQ ID NO: 37) spanning 406 bp were derived from the Genbank sequence accession number NM_010548 bases 675-1081.

The resulting amplicons were fractionated on an EtBr stained 3.0% agarose gel to determine size. Altered splicing patterns and continuity of the open reading frames were confirmed by sequencing after insertion into plasmid vector using the TOPO TA cloning kit according to manufacture's instructions (Invitrogen). At least three clones harboring the different amplicons were examined. Identity and sequence alignments were performed by BLAST search analysis.

E. Preparation of Morpholino Oligomers Having Cationic Linkages

Figure 10:
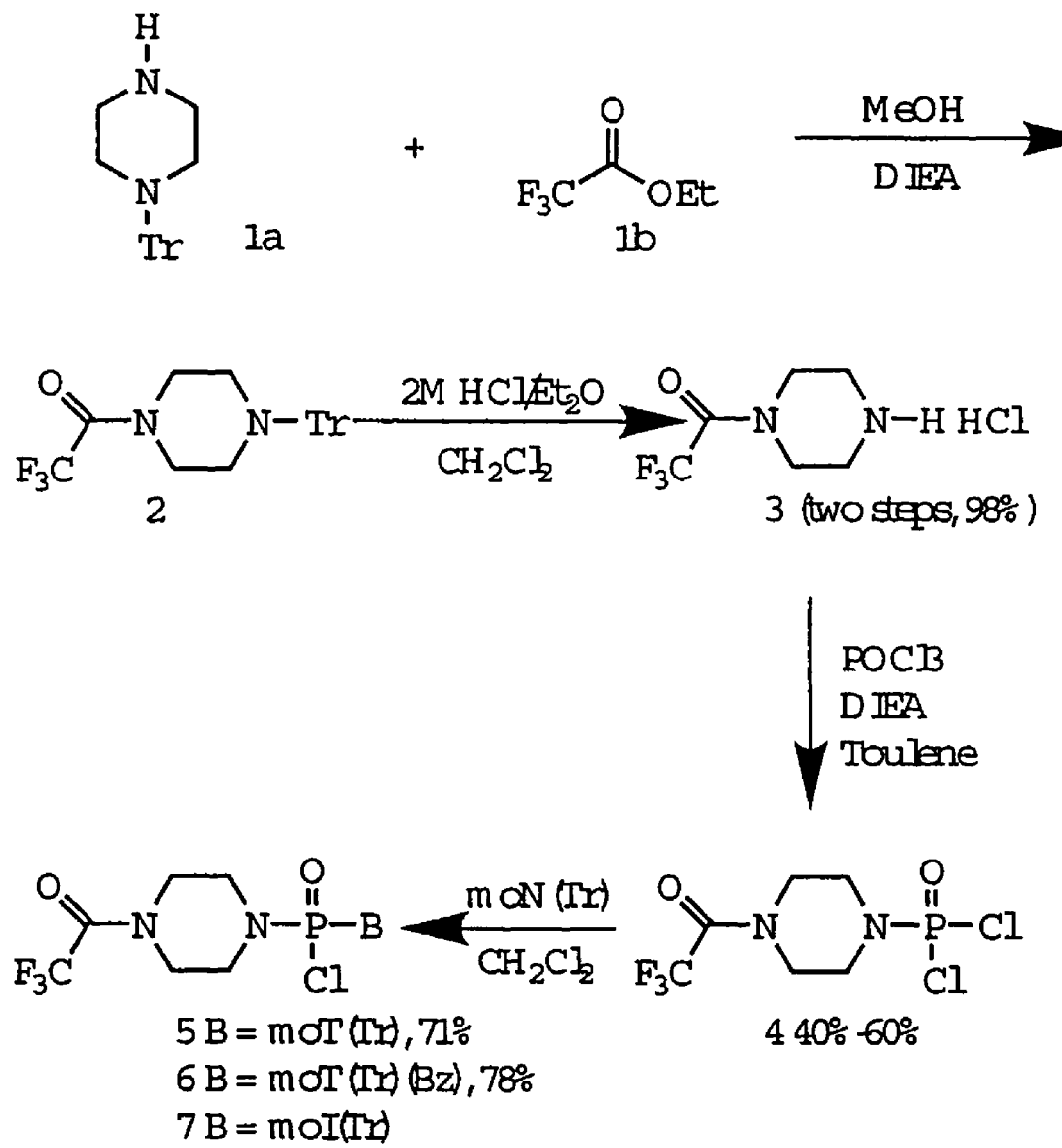
FIG. 10 shows the synthetic steps to produce subunits used to produce +PMO containing the (1-piperazino) phosphinylideneoxy cationic linkage as shown in FIG. 3H.

A schematic of a synthetic pathway that can be used to make morpholino subunits containing a (1 piperazino) phosphinylideneoxy linkage is shown in FIG. 10; further experimental detail for a representative synthesis is provided in Materials and Methods, below. As shown in the Figure, reaction of piperazine and trityl chloride gave trityl piperazine (1a), which was isolated as the succinate salt. Reaction with ethyl trifluoroacetate (1b) in the presence of a weak base (such as diisopropylethylamine or DIEA) provided 1-trifluoroacetyl-4-trityl piperazine (2), which was immediately reacted with HCl to provide the salt (3) in good yield. Introduction of the dichlorophosphoryl moiety was performed with phosphorus oxychloride in toluene.

The acid chloride (4) is reacted with morpholino subunits (moN), which may be prepared as described in U.S. Pat. No. 5,185,444 or in Summerton and Weller, 1997 (cited above), to provide the activated subunits (5, 6, 7). Suitable protecting groups are used for the nucleoside bases, where necessary; for example, benzoyl for adenine and cytosine, isobutyryl for guanine, and pivaloylmethyl for inosine. The subunits containing the (1 piperazino) phosphinylideneoxy linkage can be incorporated into the existing PMO synthesis protocol, as described, for example in Summerton and Weller (1997), without modification.

Example 1

Arginine-Rich Peptides Enhance Uptake of Oligomers into Mature Dendritic Cells

Figure 4:
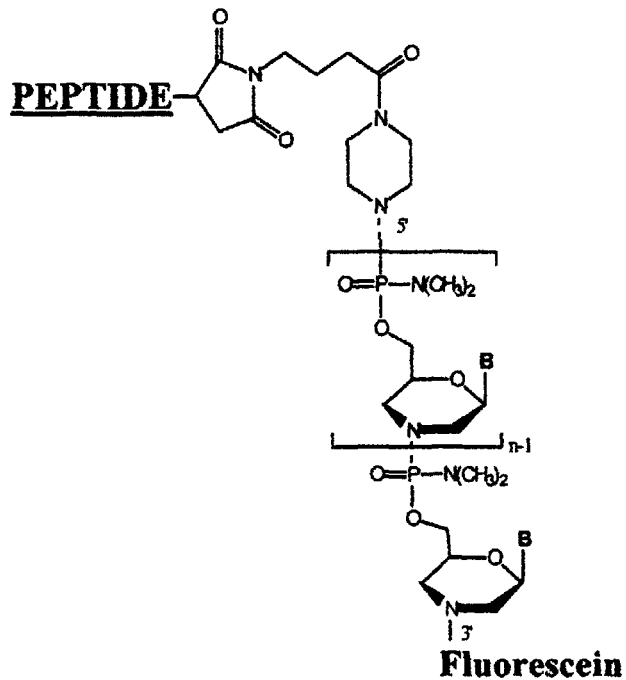
FIG. 4 shows the chemical structures of a phosphorodiamidate morpholino oligomer conjugates and the sequences of peptide conjugates used in this invention. Fluorescein can be linked to the 3' end of the peptide-PMO conjugate to allow imaging and/or detection of PMO uptake in intact cells.

Delivery of antisense molecules without substantial manipulation of the cellular membrane has been an impediment to targeting gene expression in DCs and other immune cell types. These procedures often result in extensive damage to the membrane allowing for only short lived experiments to be conducted. Numerous arginine-rich peptides were examined as to their ability to deliver oligomers to various cell types with no manipulation beyond direct addition to cells cultured under normal conditions. The PMO chemical structure and peptides used in this study are shown in FIG. 4. PMO synthesis and conjugation of peptides and or fluorescein were carried out at AVI BioPharma as previously described (Summerton and Weller 1997; Moulton, Hase et al. 2003; Moulton, Nelson et al. 2004). The arginine-rich peptides shown in FIG. 4 are among several that have been shown to enhance cellular uptake. Fluorescein can be linked to the 3' end of the peptide-PMO conjugate to allow imaging and or detection of PMO uptake in intact cells.

Using a fluorescein linked PMO, FIG. 5 shows that bone marrow derived DCs readily take up PMO conjugates of the P003 peptide (FIG. 5, SEQ ID NO:2). In the experiment represented in this figure an irrelevant control PMO (705, 5'-CCTCTTACCTCAGTTACA-3', SEQ ID NO: 31) was used to measure uptake of unconjugated and peptide-conjugated PMOs into DCs. Peptides with similar amino acid content but varied sequence such as P005 (SEQ ID NO:3) perform similarly. Surprisingly, when PMO conjugates of P002 peptide (SEQ ID NO:1) were tested it was observed that uptake into DCs was enhanced after stimulation with lipopolysaccharide (LPS) compared to untreated or immature DCs (FIG. 5).

The data presented in FIG. 5 were obtained using murine DCs obtained from murine bone marrow cells cultured for 8 days in RPMI+10% FBS supplemented with granulocyte macrophage colony stimulating factor (GM-CSF) (25 ng/ml) and treated in duplicate wells with either naked or peptide conjugated PMO 705 [5 mM] linked to fluorescein. One well for each oligomer treatment received LPS [1 mg/ml]. The cells were cultured for 16 hrs and then harvested, washed 3 times with PBS, stained with CD11c-APC and analyzed by flow cytometry. The histogram indicates the level of fluorescein in the CD11c positive (i.e. mature DC) cell population.

Example 2

Antisense Inhibition of CD86 Expression Also Alters CD80 Expression

Figure 6A:
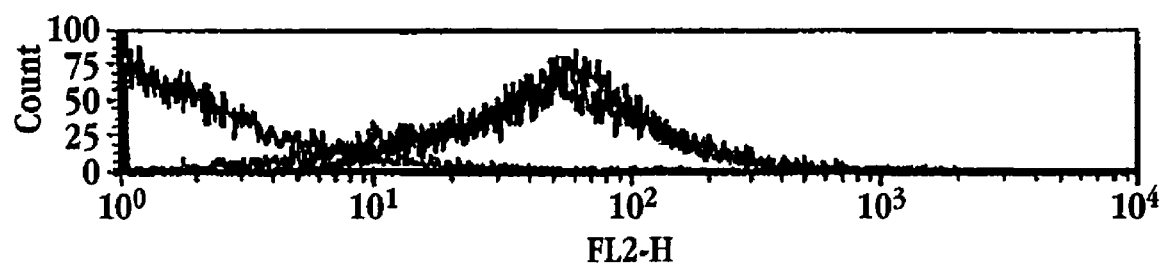
FIGS. 6A-6B show that antisense PMO to CD86 inhibits expression of both CD86 and CD80 in dendritic cells.
Figure 6B:
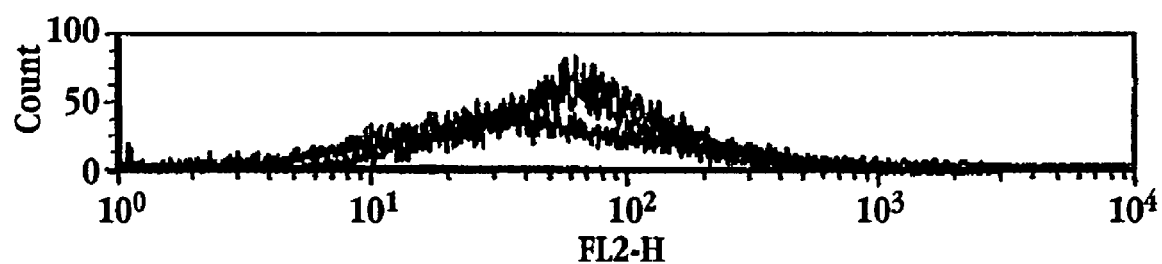

To determine if the enhanced uptake of the PMO into DCs provided by the peptide conjugates would translate into functional antisense activity we chose to synthesize oligomers targeting the translational start site of CD86 (B7-2 AUG1, SEQ ID NO:15) and a sequence scrambled control oligomer (5'-CGTGGTGCACTGCGTGTGGC-3', SEQ ID NO:30). A considerable reduction in the level of CD86 (B7-2) was observed in cultured DCs after treatment with the sequence-specific oligomer and LPS compared to controls (FIG. 6, top histogram). However, when a measure of the level of CD80 (B7-1) was made under the same conditions it was observed that a significant reduction was produced in the cultures treated with antisense to CD86 compared to controls (FIG. 6, bottom histogram). This was unexpected since the CD86 sequence shares little homology with that of CD80 and considerably low levels of homology around the translational start site. Nearly identical results were observed with regards to a reduction in CD80 when an oligomer targeting a different sequence (B7-2 AUG2, SEQ ID NO:16) surrounding the CD86 translational start site was used (data not shown).

The data in FIG. 6 were generated using bone marrow derived DCs treated in duplicate with either P002 peptide conjugated PMO [20 mM] antisense to CD86 (SEQ ID NO: 15), scrambled PMO sequence (5'-CGTGGTGCACTGCGT-GTGGC-3', SEQ ID NO:30) or media alone for 4 hours. LPS [1.0 mg/ml] was then added to all cultures for 16 hours. The cells were washed, stained with CD11c-APC antibody (i.e. specific for mature DCs) and either anti-mouse CD80-PE or CD86-PE antibodies and analyzed by flow cytometry.

Example 3

Increased DC IL-10 Production is Linked to Diminished CD86 Expression and not Ligand Interaction In light of the results seen in Example 2 we examined the cytokine production profile of the CD86 antisense treated DCs. IL-4 and IL-12 production was not significantly altered in the DCs receiving the B7-2 AUG1 CD86 antisense oligomer (SEQ ID NO:15) compared to controls (data not shown). However, IL-10 production was evident when DCs were treated with a maturation stimulus such as LPS in conjunction with the CD86 antisense oligomer-P002 conjugate (SEQ ID NO:15) and not the P002 peptide alone or a scrambled control sequence conjugated to P002 as shown in Table 3 below. The same result was seen when other delivery peptides were used with SEQ ID NO:15 or alternate sequences targeting the translational start site (SEQ ID NO:16). Furthermore, IL-10 staining was detectable when the DCs were not permeabilized indicating that IL-10 was being secreted from the cells where it could exert an autocrine or paracrine effect (data not shown).

TABLE 3

Inhibition of CD86 Induces IL-10 Production in
LPS-treated Dendritic Cells

| Treatment | % DCs CD86 Positive | % DCs IL10 Positive |
|---|---|---|
| Control (No LPS) | 6.92 | 0.10 |
| P002 Peptide (No LPS) | 6.47 | 0.10 |
| Scramble-P002 +LPS | 13.4 | 0.75 |
| B7-2 AUG1(SEQ ID NO: 15)-P002(SEQ ID NO: 1) +LPS | 2.26 | 21.1 |

The data presented in Table 3 was generated using murine bone marrow derived DCs treated in duplicate with either P002 peptide (SEQ ID NO:1) alone, P002 conjugated to PMO antisense CD86 (SEQ ID NO:15) or scrambled PMO sequence (5'-CGTGGTGCACTGCGTGTGGC-3', SEQ ID NO:30) at 20 mM or media alone for 4 hours. LPS [1.0 mg/ml] was then added to the appropriate cultures for 16 hours. The cell were washed, FC blocked, then stained with antibody specific for mature DCs (CD11c-APC) and antibody specific for CD86 (CD86-PE). Intracellular staining with anti-IL-10-FITC antibody was carried out after fixation and permeabilization of the cells. The numbers indicate the percentage of CD11c positive cells (mature DCs) staining positive for IL-10 and CD86 respectively.

We also examined whether the regulation of IL-10 in the mature DCs was due to the loss of some interaction with a yet unknown ligand that is present in bone marrow derived DCs cultures or whether it might be due to the loss of control through the absences of CD86 (B7-2). A recombinant form of the CTLA-4 molecule, a receptor on T cells for CD86, was used to block interactions of the CD86 molecule in cultured DCs. DCs receiving this treatment were compared to CD86 antisense-treated DCs as to the levels of IL-10 produced under two different conditions of DCs maturation. DCs received a maturation stimulus from either LPS or anti-CD40 and were then stained for intracellular IL-10. Under either maturation condition IL-10 was only significantly produced in the P002-conjugated CD86 antisense (SEQ ID NO: 15) treated cells compared to control untreated cells (FIG. 7). This suggests that the regulation of IL-10 production in maturing DCs is linked to levels of CD86 expression and not those of CD86 interactions with a ligand.

The data in FIG. 7, which shows blocking CD86 interactions does not lead to IL-10 expression in bone marrow derived DCs, were generated by treatment of murine bone marrow DCs in duplicate with either media alone, antisense CD86-P003 conjugate [2 mM] or CTLA4 Ig [5.0 mg/ml] for 4 hours. One of the duplicate cultures was treated with LPS [1.0 mg/ml] and the other with anti-CD40 [5.0 mg/ml] for 16 hours to induce maturation. The cells were washed, FC blocked, surface stained for CD11c-APC, fixed and permeabilized for intracellular staining with anti-IL-10 FITC. Samples were analyzed by flow cytometry gating on CD11c positive cells.

Example 4

Regulation of IL-10 Production in Mature DCs Controlled Through CD86 Exon 10

To further examine the question regarding the role of CD86 in the regulation of IL-10 production in maturing DCs we determined what components of the CD86 polypeptide might be responsible. The approach taken was to systematically alter the CD86 protein by limiting expression of either intracellular or extracellular polypeptide domains. This was done by using antisense oligomers with sequences targeting splice sites within the unprocessed message thereby forcing alterations in the mature message to exclude particular exons (Target and targeting sequences are shown in Table 1 and Table 2, respectively).

Employing RT-PCR on total RNA isolated from murine DCs treated with the different oligomers shows that the predicted alterations to the CD86 mRNA could be achieved (FIGS. 8A and 8B). Some cloned sequences exhibited an alternative splice acceptor site in Exon 8 which has been shown to be used in normal APCs (Borriello, Oliveros et al. 1995).

The data in FIGS. 8A and 8B demonstrate that antisense targeting of splice donor or splice acceptor sites alters CD86 mRNA. The data were generated using bone marrow derived DCs treated with [10 mM] of either P002-CD86 (SEQ ID NO:15) antisense PMO or scramble PMO peptide conjugates or P005 PMO peptide conjugates targeting splice junction sites for exons 7, 9, 10 and 11 (SEQ ID NOS: 17, 18, 19 and 20, respectively) for 4 hours and then treated for 16 hours with LPS [1.0 mg/ml]. Total RNA was isolated from each culture, treated with DNAse free RNAse and used as template material for single-tube reverse transcription and polymerase chain reaction using primers spanning an 870 base pair region on the CD86 mRNA. As shown in FIG. 8A, the reaction material was fractionated on an EtBr stained 3.0% agarose gel to determine the size of the resulting amplicons. FIG. 8B shows a schematic of the altered splicing patterns that were observed. The continuity of the open reading frames were confirmed by sequencing various clones of the amplicons after insertion into plasmid DNA vector. A schematic representation of some of the cloned sequences is shown in FIG. 8B by lines aligned with the wild type CD86 map. The intervening black lines depict regions where splicing was altered. The relative positions of the PMOs and the PCR primers are also shown.

Example 5

Figure 9A:
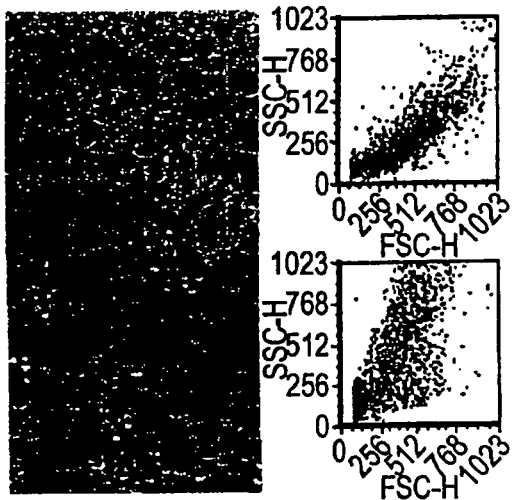
FIGS. 9A-9C demonstrate that antisense PMO targeted to the CD86 start codon or Exon 10 of the CD86 gene alters the morphology of the lipopolysaccharide-treated dendritic cells.
Figure 9B:
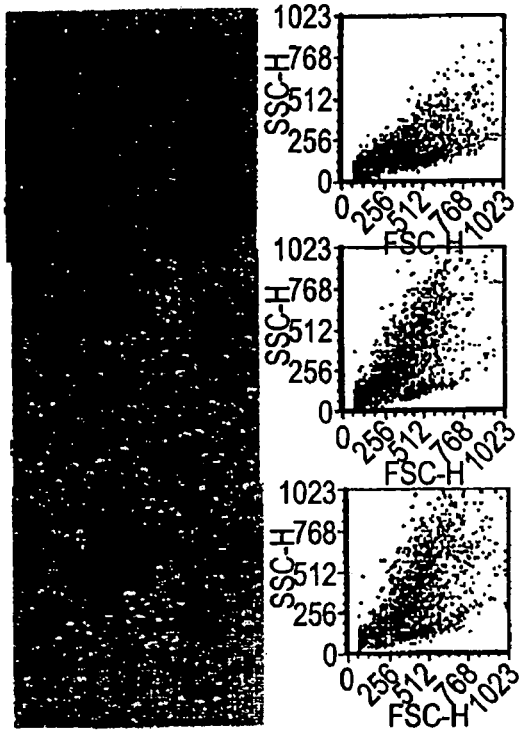
Figure 9C:
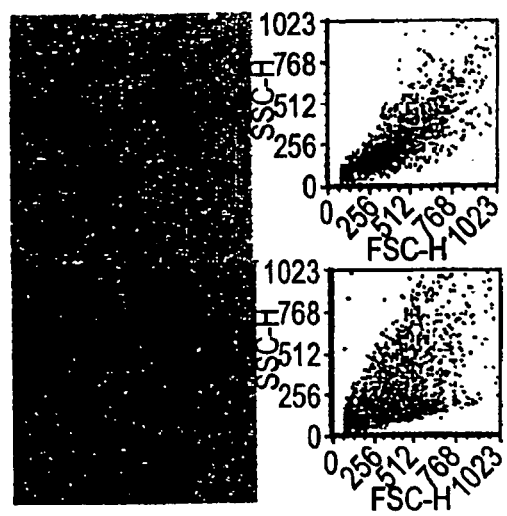

Inhibition of CD86 or CD86 Exon 10 Expression Alters Morphology of LPS-Treated DCs In addition to molecular evidence of the effect of the splice altering oligomers as described in Example 4, phenotypic changes in the treated DCs were also observed. Specifically, DCs treated with the Exon 10 antisense oligomer (SEQ ID NO: 19) exhibited the greatest production of IL-10 and maintained an immature phenotype when exposed to LPS (Table 4, below and FIG. 9, respectively). Table 4, shows that antisense PMO designed to block Exon 10 expression induces IL-10 in mature dendritic cells. FIG. 9 shows that inhibition of CD86 or Exon 10 expression alters the morphology of LPS treated DCs. In this experiment, bone marrow derived DCs were treated as previously described in Example 4. Prior to staining for flow cytometry the cultured DCs were imaged by light microscopy. The forward and side light scattering properties of each culture are shown to the right of each image.

TABLE 4

Exon 10 of the CD86 Gene Regulates IL-10 production in Mature Dendritic Cells

| Treatment | % DCs CD86 Positive | % DCs IL10 Positive |
|---|---|---|
| Control | 10.40 | 0.30 |
| Control (+LPS) | 33.81 | 0.07 |
| B7-2 AUG (SEQ ID NO: 15) +LPS | 17.93 | 2.06 |
| EXON 9sd (SEQ ID NO: 18) +LPS | 26.62 | 1.48 |
| EXON 10sa (SEQ ID NO: 19) +LPS | 13.36 | 4.04 |
| EXON 11sa (SEQ ID NO: 20) +LPS | 5.06 | 0.65 |

| Name | Sequence (5' TO 3') | SEQ ID NO |
|---|---|---|
| P002 | N-RRRQRRKKRGYC-CONH$_2$ | 1 |
| P003 | N-RRRRRRRRRFFC-CONH$_2$ | 2 |
| P005 | N-RRRQRRKKRGYFFC-CONH$_2$ | 3 |
| B7-2 AUG | Cggaagcacccacgatggaccccag | 4 |
| Exon 7sa | Gctgtttccgtggagacgc | 5 |
| Exon 9sd | Gccgaatcagcttagcagg | 6 |
| Exon 10sa | Gcccagcaacacagcctct | 7 |
| Exon 11sa | Gaaaccaaatgcagagtg | 8 |
| CD86 AUG | catttgtgacagcactatgggactgagtaacattctctttgtgatg | 9 |
| CD86Ex6sa | Agcttgaggaccctcagcctc | 10 |
| CD86Ex6sd | Gcctcgcaactcttataaatgtg | 11 |
| CD86Ex7sa | Gaaccaacacaatggagaggga | 12 |
| CD86Ex7sd | Gagtgaacagaccaagaaaag | 13 |
| CD86Ex8sa | Agaaaaaatccatatacctgaa | 14 |
| B7-2 AUG1 | 5'-CTGGGGTCCATCGTGGGTGC-3' | 15 |
| B7-2 AUG2 | 5'-GGGGTCCATCGTGGGTGCTTCCG-3' | 16 |
| Exon 7sa | 5'-GCGTCTCCACGGAAACAGC-3' | 17 |
| Exon 9sd | 5'-CCTGCTAAGCTGATTCGGC-3' | 18 |
| Exon 10sa | 5'-AGAGGCTGTGTTGCTGGGC-3' | 19 |
| Exon 11sa | 5'-CACTCTGCATTTGGTTTC-3' | 20 |
| CD86 AUG1 | 5'-GTTACTCAGTCCCATAGTGCTG-3' | 21 |
| CD86 AUG2 | 5'-CCATAGTGCTGTCACAAATG-3' | 22 |
| CD86 AUG3 | 5'-GAATGTTACTCAGTCCCATAG-3' | 23 |
| CD86Ex6sa | 5'-GAGGCTGAGGGTCCTCAAGCT-3' | 24 |
| CD86Ex6sd | 5'-CACATTTATAAGAGTTGCGAGGC-3' | 24 |
| CD86Ex7sa | 5'-'TCCCTCTCCATTGTGTTGGTTC-3' | 24 |
| CD86Ex7sd | 5'-CTTTTCTTGGTCTGTTCACTC-3' | 27 |
| CD86Ex8sa | 5'-TTCAGGTATATGGATTTTTCT-3' | 28 |
| B7-1 AUG | 5'-GCAAGCCATAGCTTCAGATGC-3' | 29 |

-continued

| Name | Sequence (5' TO 3') | SEQ ID NO |
|---|---|---|
| Scramble | 5'-CGTGGTGCACTGCGTGTGGC-3' | 30 |
| 705-FL | 5'-CCTCTTACCTCAGTTACA-FL-3' | 31 |
| CD86 AUG4 | 5'-CATCACAAAGAGAATGTTACTC-3' | 32 |

SEQ ID NO: 33
Human CD86 mRNA
>gi|29029570|ref|NM_006889.2| Homo sapiens CD86 antigen
(CD28 antigen ligand 2, B7-2 antigen) (CD86), transcript
variant 2, mRNA
AGGAGCCTTAGGAGGTACGGGGAGCTCGCAAATACTCCTTTTGGTTTATTCTTACC

ACCTTGCTTCTGTGTTCCTTGGGAATGCTGCTGTGCTTATGCATCTGGTCTCTTTTT

GGAGCTAGAGTGGACAGGCATTTGTGACAGCACTATGGGACTGAGTAACATTCTCT

TTGTGATGGCCTTCCTGCTCTCTGGTGCTGCTCCTCTGAAGATTCAAGCTTATTTCA

ATGAGACTGCAGACCTGCCATGCCAATTTGCAAACTCTCAAAACCAAAGCCTGAGT

GAGCTAGTAGTATTTTGGCAGGACCAGGAAAACTTGGTTCTGAATGAGGTATACTT

AGGCAAAGAGAAATTTGACAGTGTTCATTCCAAGTATATGGGCCGCACAAGTTTTG

ATTCGGACAGTTGGACCCTGAGACTTCACAATCTTCAGATCAAGGACAAGGGCTTG

TATCAATGTATCATCCATCACAAAAAGCCCACAGGAATGATTCGCATCCACCAGAT

GAATTCTGAACTGTCAGTGCTTGCTAACTTCAGTCAACCTGAAATAGTACCAATTTC

TAATATAACAGAAAATGTGTACATAAATTTGACCTGCTCATCTATACACGGTTACCC

AGAACCTAAGAAGATGAGTGTTTTGCTAAGAACCAAGAATTCAACTATCGAGTATG

ATGGTATTATGCAGAAATCTCAAGATAATGTCACAGAACTGTACGACGTTTCCATCA

GCTTGTCTGTTTCATTCCCTGATGTTACGAGCAATATGACCATCTTCTGTATTCTGG

AAACTGACAAGACGCGGCTTTTATCTTCACCTTTCTCTATAGAGCTTGAGGACCCT

CAGCCTCCCCCAGACCACATTCCTTGGATTACAGCTGTACTTCCAACAGTTATTATA

TGTGTGATGGTTTTCTGTCTAATTCTATGGAAATGGAAGAAGAAGAAGCGGCCTCG

CAACTCTTATAAATGTGGAACCAACACAATGGAGAGGGAAGAGAGTGAACAGACC

AAGAAAAGAGAAAAAATCCATATACCTGAAAGATCTGATGAAGCCGAGCGTGTTTT

TAAAAGTTCGAAGACATCTTCATGCGACAAAAGTGATACATGTTTTTAATTAAAGAG

TAAAGCCCATACAAGTATTCATTTTTTCTACCCTTTCCTTTGTAAGTTCCTGGGCAA

CCTTTTTGATTTCTTCCAGAAGGCAAAAGACATTACCATGAGTAATAAGGGGGCT

CCAGGACTCCCTCTAAGTGGAATAGCCTCCCTGTAACTCCAGCTCTGCTCCGTATG

CCAAGAGGAGACTTTAATTCTCTTACTGCTTCTTTTCACTTCAGAGCACACTTATGG

GCCAAGCCCAGCTTAATGGCTCATGACCTGGAAATAAAATTTAGGACCAATACCTC

CTCCAGATCAGATTCTTCTCTTAATTTCATAGATTGTGTTTTTTTTAAATAGACCTC

TCAATTTCTGGAAAACTGCCTTTTATCTGCCCAGAATTCTAAGCTGGTGCCCCACTG

AATCTTGTGTACCTGTGACTAAACAACTACCTCCTCAGTCTGGGTGGGACTTATGT

ATTTATGACCTATAGTGTTAATATCTTGAAACATAGAGATCTATGTACTGTAATAGT

GTGATTACTATGCTCTAGAGAAAAGTCTACCCCTGCTAAGGAGTTCTCATCCCTCT

GTCAGGGTCAGTAAGGAAAACGGTGGCCTAGGGTACAGGCAACAATGAGCAGAC

CAACCTAAATTTGGGGAAATTAGGAGAGGCAGAGATAGAACCTGGAGCCACTTCTA

TCTGGGCTGTTGCTAATATTGAGGAGGCTTGCCCCACCCAACAAGCCATAGTGGA

| Name | Sequence (5' TO 3') | SEQ ID NO |
|---|---|---|
| | GAGAACTGAATAAACAGGAAAATGCCAGAGCTTGTGAACCCTGTTTCTCTTGAAGA | |
| | ACTGACTAGTGAGATGGCCTGGGGAAGCTGTGAAAGAACCAAAAGAGATCACAAT | |
| | ACTCAAAAGAGAGAGAGAGAGAAAAAAGAGAGATCTTGATCCACAGAAATACATGA | |
| | AATGTCTGGTCTGTCCACCCCATCAACAAGTCTTGAAACAAGCAACAGATGGATAG | |
| | TCTGTCCAAATGGACATAAGACAGACAGCAGTTTCCCTGGTGGTCAGGGAGGGGT | |
| | TTTGGTGATACCCAAGTTATTGGGATGTCATCTTCCTGGAAGCAGAGCTGGGGAG | |
| | GGAGAGCCATCACCTTGATAATGGGATGAATGGAAGGAGGCTTAGGACTTTCCAC | |
| | TCCTGGCTGAGAGAGGAAGAGCTGCAACGGAATTAGGAAGACCAAGACACAGATC | |
| | ACCCGGGGCTTACTTAGCCTACAGATGTCCTACGGGAACGTGGGCTGGGCCAGCA | |
| | TAGGGCTAGCAAATTTGAGTTGGATGATTGTTTTGCTCAAGGCAACCAGAGGAAA | |
| | CTTGCATACAGAGACAGATATACTGGGAGAAATGACTTTGAAAACCTGGCTCTAAG | |
| | GTGGGATCACTAAGGGATGGGCAGTCTCTGCCCAAACATAAAGAGAACTCTGGG | |
| | GAGCCTGAGCCACAAAAATGTTCCTTTATTTTATGTAAACCCTCAAGGGTTATAGAC | |
| | TGCCATGCTAGACAAGCTTGTCCATGTAATATTCCCATGTTTTTACCCTGCCCCTGC | |
| | CTTGATTAGACTCCTAGCACCTGGCTAGTTTCTAACATGTTTTGTGCAGCACAGTTT | |
| | TTAATAAATGCTTGTTACATTC | |

It is claimed:

1. A method of inducing increased production of extracellular IL-10 in mature dendritic cells, comprising
   (a) exposing a population of human dendritic cells that includes mature dendritic cells to an antisense compound composed of phosphorus-containing intersubunit linkages joining a morpholino nitrogen of one subunit to a 5' exocyclic carbon of an adjacent subunit and containing 12-40 subunits, including a base sequence of at least 12 contiguous bases that are complementary to a target region within the sequence identified by SEQ ID NO:9, wherein said compound is covalently linked, at one compound end, to an arginine-rich peptide effective to enhance uptake of said compound into the mature dendritic cells, and
   (b) by said exposing in step (a), blocking expression of full-length CD86 in said cells,
   (c) by said blocking, thereby producing inhibition of the expression of full-length CD86 on the surface of mature dendritic cells, and enhanced expression of extracellular IL-10 by mature dendritic cells.

2. The method of claim 1, wherein the morpholino subunits in the compound to which the dendritic cells are exposed are joined by phosphorodiamidate linkages, in accordance with the structure:

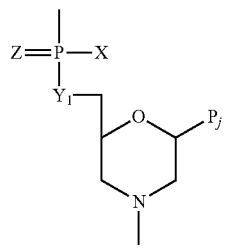

where $Y_1$=O, Z=O, Pj is a purine or pyrimidine base-pairing moiety effective to bind, by base-specific hydrogen bonding, to a base in a polynucleotide, and X is alkyl, alkoxy, thioalkoxy, amino or alkyl amino, and said heteroduplex structure formed in step (a) has a Tm of at least 50° C.

3. The method of claim 1, in which at least 2 and no more than half of the total number of intersubunit linkages are cationic linkages, wherein said morpholino subunits are joined by phosphorodiamidate linkages, in accordance with the structure:

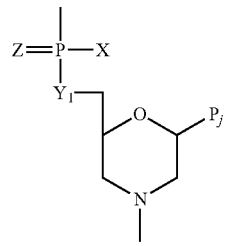

where $Y_1$=a, Z=O, Pj is a purine or pyrimidine base-pairing moiety effective to bind, by base-specific hydrogen bonding, to a base in a polynucleotide, and X for the uncharged linkages is alkyl, alkoxy, thioalkoxy, or an alkyl amino of the form $NR_2$, where each R is independently hydrogen or methyl, and for the cationic linkages, X is 1-piperazine.

4. The method of claim 2, wherein X=$NR_2$, where each R is independently hydrogen or methyl in the compound to which the T cells are exposed.

5. The method of claim 1, wherein said arginine-rich peptide has a sequence selected from the group consisting of SEQ ID NOS: 1 and 2.

6. The method of claim 1, wherein said dendritic cells which are exposed to said compound include a mixture of immature and mature dendritic cells, said compound is covalently linked to an arginine-rich rTAT peptide having the sequence identified by SEQ ID NO: 1, and the rTAT peptide is effective to achieve a greater level of intracellular uptake of the antisense compound into the mature dendritic cells than is achieved (i) in the immature dendritic cells, or (ii) by exposing the mature dendritic cells to the antisense compound in the absence of the rTAT polypeptide.

7. The method of claim 1, wherein the antisense compound includes a base sequence selected from the group consisting of: SEQ ID NOS:21-23 and 32.

8. The method of claim 1, for use in inhibiting transplantation rejection in a human subject receiving an allograft tissue or organ, wherein said exposing includes administering the antisense compound to the subject, in an amount effective to inhibit the rate and extent of rejection of the transplant.

9. The method of claim 8, wherein said administering is carried out both prior to and following the allograft tissue or organ transplantation in the subject.

10. The method of claim 8, wherein said administering is carried out for a selected period of 1-3 weeks.

11. The method of claim 10, which further includes further administering the antisense compound to the subject, as needed, to control the extent of transplantation rejection in the subject.

12. The method of claim 1, for use in treating an autoimmune condition in a human subject, wherein said exposing includes administering the antisense compound to the subject, in an amount effective to reduce the severity of the autoimmune condition.

13. The method of claim 12, wherein said administering is carried out over an extended period of time, as needed, to control the severity of the autoimmune condition in the subject.

14. A method of inducing mature human dendritic cells to a condition of increased production of extracellular IL-10, comprising
 (a) exposing a population of human dendritic cells that comprises mature dendritic cells to an antisense compound composed of phosphorus-containing intersubunit linkages joining a morpholino nitrogen of one subunit to a 5' exocyclic carbon of an adjacent subunit and containing 12-40 subunits, including a base sequence of at least 12 contiguous bases that are complementary to a target region within the sequence identified by SEQ ID NO:9, wherein said compound is covalently linked to an arginine-rich rTAT peptide having the sequence identified by SEQ ID NO: 1, and
 (b) by said exposing in step (a), blocking expression of full-length CD86 in said cells,
 (c) thereby enhancing expression of extracellular IL-10 by the mature dendritic cells.

* * * * *

SEQUENCE LISTING

<160> NUMBER OF SEQ ID NOS: 37

<210> SEQ ID NO 1
<211> LENGTH: 12
<212> TYPE: PRT
<213> ORGANISM: Artificial Sequence
<220> FEATURE:
<223> OTHER INFORMATION: The reverse of a TAT sequence from the Human
      immunodeficiency virus type 1

<400> SEQUENCE: 1

Arg Arg Arg Gln Arg Arg Lys Lys Arg Gly Tyr Cys
1               5                   10

<210> SEQ ID NO 2
<211> LENGTH: 12
<212> TYPE: PRT
<213> ORGANISM: Artificial Sequence
<220> FEATURE:
<223> OTHER INFORMATION: Synthetic Arginine-rich peptide

<400> SEQUENCE: 2

Arg Arg Arg Arg Arg Arg Arg Arg Arg Phe Phe Cys
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic Arginine-rich peptide

<400> SEQUENCE: 3

Arg Arg Arg Gln Arg Arg Lys Lys Arg Gly Tyr Phe Phe Cys
1               5                   10

<210> SEQ ID NO 4
<211> LENGTH: 25
<212> TYPE: DNA
<213> ORGANISM: Mus musculus

<400> SEQUENCE: 4
cggaagcacc cacgatggac cccag                                         25

<210> SEQ ID NO 5
<211> LENGTH: 19
<212> TYPE: DNA
<213> ORGANISM: Mus musculus

<400> SEQUENCE: 5
gctgtttccg tggagacgc                                                19

<210> SEQ ID NO 6
<211> LENGTH: 19
<212> TYPE: DNA
<213> ORGANISM: Mus musculus

<400> SEQUENCE: 6
gccgaatcag cttagcagg                                                19

<210> SEQ ID NO 7
<211> LENGTH: 19
<212> TYPE: DNA
<213> ORGANISM: Mus musculus

<400> SEQUENCE: 7
gcccagcaac acagcctct                                                19

<210> SEQ ID NO 8
<211> LENGTH: 18
<212> TYPE: DNA
<213> ORGANISM: Mus musculus

<400> SEQUENCE: 8
gaaaccaaat gcagagtg                                                 18

<210> SEQ ID NO 9
<211> LENGTH: 46
<212> TYPE: DNA
<213> ORGANISM: Homo sapiens

<400> SEQUENCE: 9
catttgtgac agcactatgg gactgagtaa cattctcttt gtgatg                  46

<210> SEQ ID NO 10
<211> LENGTH: 21
<212> TYPE: DNA
<213> ORGANISM: Homo sapiens

<400> SEQUENCE: 10
agcttgagga ccctcagcct c                                             21

<210> SEQ ID NO 11
<211> LENGTH: 23
<212> TYPE: DNA

<213> ORGANISM: Homo sapiens

<400> SEQUENCE: 11
gcctcgcaac tcttataaat gtg                                    23

<210> SEQ ID NO 12
<211> LENGTH: 22
<212> TYPE: DNA
<213> ORGANISM: Homo sapiens

<400> SEQUENCE: 12
gaaccaacac aatggagagg ga                                     22

<210> SEQ ID NO 13
<211> LENGTH: 21
<212> TYPE: DNA
<213> ORGANISM: Homo sapiens

<400> SEQUENCE: 13
gagtgaacag accaagaaaa g                                      21

<210> SEQ ID NO 14
<211> LENGTH: 22
<212> TYPE: DNA
<213> ORGANISM: Homo sapiens

<400> SEQUENCE: 14
agaaaaaatc catatacctg aa                                     22

<210> SEQ ID NO 15
<211> LENGTH: 20
<212> TYPE: DNA
<213> ORGANISM: Artificial Sequence
<220> FEATURE:
<223> OTHER INFORMATION: synthetic antisense oligomer sequence directed
      against SEQ ID NO:4

<400> SEQUENCE: 15
ctggggtcca tcgtgggtgc                                        20

<210> SEQ ID NO 16
<211> LENGTH: 23
<212> TYPE: DNA
<213> ORGANISM: Artificial Sequence
<220> FEATURE:
<223> OTHER INFORMATION: synthetic antisense oligomer sequence directed
      against SEQ ID NO:4

<400> SEQUENCE: 16
ggggtccatc gtgggtgctt ccg                                    23

<210> SEQ ID NO 17
<211> LENGTH: 19
<212> TYPE: DNA
<213> ORGANISM: Artificial Sequence
<220> FEATURE:
<223> OTHER INFORMATION: synthetic antisense oligomer sequence directed
      against SEQ ID NO:5

<400> SEQUENCE: 17
gcgtctccac ggaaacagc                                         19

<210> SEQ ID NO 18
<211> LENGTH: 19
<212> TYPE: DNA
<213> ORGANISM: Artificial Sequence

```
<220> FEATURE:
<223> OTHER INFORMATION: synthetic antisense oligomer sequence directed
      against SEQ ID NO:6

<400> SEQUENCE: 18
cctgctaagc tgattcggc                                                    19

<210> SEQ ID NO 19
<211> LENGTH: 19
<212> TYPE: DNA
<213> ORGANISM: Artificial Sequence
<220> FEATURE:
<223> OTHER INFORMATION: synthetic antisense oligomer sequence directed
      against SEQ ID NO:7

<400> SEQUENCE: 19
agaggctgtg ttgctgggc                                                    19

<210> SEQ ID NO 20
<211> LENGTH: 18
<212> TYPE: DNA
<213> ORGANISM: Artificial Sequence
<220> FEATURE:
<223> OTHER INFORMATION: synthetic antisense oligomer sequence directed
      against SEQ ID NO:8

<400> SEQUENCE: 20
cactctgcat ttggtttc                                                     18

<210> SEQ ID NO 21
<211> LENGTH: 22
<212> TYPE: DNA
<213> ORGANISM: Artificial Sequence
<220> FEATURE:
<223> OTHER INFORMATION: synthetic antisense oligomer sequence directed
      against SEQ ID NO:9

<400> SEQUENCE: 21
gttactcagt cccatagtgc tg                                                22

<210> SEQ ID NO 22
<211> LENGTH: 20
<212> TYPE: DNA
<213> ORGANISM: Artificial Sequence
<220> FEATURE:
<223> OTHER INFORMATION: synthetic antisense oligomer sequence directed
      against SEQ ID NO:9

<400> SEQUENCE: 22
ccatagtgct gtcacaaatg                                                   20

<210> SEQ ID NO 23
<211> LENGTH: 21
<212> TYPE: DNA
<213> ORGANISM: Artificial Sequence
<220> FEATURE:
<223> OTHER INFORMATION: synthetic antisense oligomer sequence directed
      against SEQ ID NO:9

<400> SEQUENCE: 23
gaatgttact cagtcccata g                                                 21

<210> SEQ ID NO 24
<211> LENGTH: 21
<212> TYPE: DNA
<213> ORGANISM: Artificial Sequence
<220> FEATURE:
<223> OTHER INFORMATION: synthetic antisense oligomer sequence directed
```

```
                                   against SEQ ID NO:10

<400> SEQUENCE: 24
gaggctgagg gtcctcaagc t                                                     21

<210> SEQ ID NO 25
<211> LENGTH: 23
<212> TYPE: DNA
<213> ORGANISM: Artificial Sequence
<220> FEATURE:
<223> OTHER INFORMATION: synthetic antisense oligomer sequence directed
      against SEQ ID NO:11

<400> SEQUENCE: 25
cacatttata agagttgcga ggc                                                   23

<210> SEQ ID NO 26
<211> LENGTH: 22
<212> TYPE: DNA
<213> ORGANISM: Artificial Sequence
<220> FEATURE:
<223> OTHER INFORMATION: synthetic antisense oligomer sequence directed
      against SEQ ID NO:12

<400> SEQUENCE: 26
tccctctcca ttgtgttggt tc                                                    22

<210> SEQ ID NO 27
<211> LENGTH: 21
<212> TYPE: DNA
<213> ORGANISM: Artificial Sequence
<220> FEATURE:
<223> OTHER INFORMATION: synthetic antisense oligomer sequence directed
      against SEQ ID NO:13

<400> SEQUENCE: 27
cttttcttgg tctgttcact c                                                     21

<210> SEQ ID NO 28
<211> LENGTH: 22
<212> TYPE: DNA
<213> ORGANISM: Artificial Sequence
<220> FEATURE:
<223> OTHER INFORMATION: synthetic antisense oligomer sequence directed
      against SEQ ID NO:14

<400> SEQUENCE: 28
ttcaggtata tggatttttt ct                                                    22

<210> SEQ ID NO 29
<211> LENGTH: 21
<212> TYPE: DNA
<213> ORGANISM: Artificial Sequence
<220> FEATURE:
<223> OTHER INFORMATION: synthetic antisense oligomer sequence directed
      against the start site of mouse B7-1 transcript

<400> SEQUENCE: 29
gcaagccata gcttcagatg c                                                     21

<210> SEQ ID NO 30
<211> LENGTH: 20
<212> TYPE: DNA
<213> ORGANISM: Artificial Sequence
<220> FEATURE:
<223> OTHER INFORMATION: synthetic scrambled antisense oligomer sequence

<400> SEQUENCE: 30
```

```
cgtggtgcac tgcgtgtggc                                                 20

<210> SEQ ID NO 31
<211> LENGTH: 18
<212> TYPE: DNA
<213> ORGANISM: Artificial Sequence
<220> FEATURE:
<223> OTHER INFORMATION: synthetic antisense oligomer sequence
      conjugated to fluorescein at the 3' end and directed against human
      b-globin intron 2

<400> SEQUENCE: 31
cctcttacct cagttaca                                                   18

<210> SEQ ID NO 32
<211> LENGTH: 22
<212> TYPE: DNA
<213> ORGANISM: Artificial Sequence
<220> FEATURE:
<223> OTHER INFORMATION: synthetic antisense oligomer sequence directed
      against the start site of human CD86 transcript

<400> SEQUENCE: 32
catcacaaag agaatgttac tc                                              22

<210> SEQ ID NO 33
<211> LENGTH: 2717
<212> TYPE: DNA
<213> ORGANISM: Homo sapiens

<400> SEQUENCE: 33
aggagcctta ggaggtacgg ggagctcgca aatactcctt ttggtttatt cttaccacct     60
tgcttctgtg ttccttggga atgctgctgt gcttatgcat ctggtctctt tttggagcta    120
cagtggacag gcatttgtga cagcactatg ggactgagta acattctctt tgtgatggcc    180
ttcctgctct ctggtgctgc tcctctgaag attcaagctt atttcaatga gactgcagac    240
ctgccatgcc aatttgcaaa ctctcaaaac caaagcctga gtgagctagt agtattttgg    300
caggaccagg aaaacttggt tctgaatgag gtatacttag gcaaagagaa atttgacagt    360
gttcattcca gtatatgggg ccgcacaagt tttgattcgg acagttggac cctgagactt    420
cacaatcttc agatcaagga caagggcttg tatcaatgta tcatccatca caaaaagccc    480
acaggaatga ttcgcatcca ccagatgaat tctgaactgt cagtgcttgc taacttcagt    540
caacctgaaa tagtaccaat ttctaatata acagaaaatg tgtacataaa tttgacctgc    600
tcatctatac acggttaccc agaacctaag aagatgagtg ttttgctaag aaccaagaat    660
tcaactatcg agtatgatgg tattatgcag aaatctcaag ataatgtcac agaactgtac    720
gacgtttcca tcagcttgtc tgtttcattc cctgatgtta cgagcaatat gaccatcttc    780
tgtattctgg aaactgacaa gacgcggctt ttatcttcac cttctctat agagcttgag    840 gaccctcagc ctcccccaga ccacattcct tggattacag ctgtacttcc aacagttatt    900
atatgtgtga tggtttttctg tctaattcta tggaaatgga agaagaagaa gcggcctcgc    960
aactcttata atgtggaac caacacaatg gagagggaag agagtgaaca gaccaagaaa   1020
agagaaaaaa tccatatacc tgaaagatct gatgaagccc agcgtgtttt taaaagttcg   1080
aagacatctt catgcgacaa aagtgataca tgttttttaat taaagagtaa agcccataca   1140
agtattcatt ttttctaccc tttccttttgt aagttcctgg gcaaccttt tgatttcttc   1200 cagaaggcaa aagacatta ccatgagtaa taaggggggct ccaggactcc ctctaagtgg   1260
```

```
aatagcctcc ctgtaactcc agctctgctc cgtatgccaa gaggagactt taattctctt    1320
actgcttctt ttcacttcag agcacactta tgggccaagc ccagcttaat ggctcatgac    1380
ctggaaataa aatttaggac caataccctcc tccagatcag attcttctct taatttcata   1440
gattgtgttt tttttaaat agacctctca atttctggaa aactgccttt tatctgccca    1500
gaattctaag ctggtgcccc actgaatctt gtgtacctgt gactaaacaa ctacctcctc    1560
agtctgggtg ggacttatgt atttatgacc ttatagtgtt aatatcttga aacatagaga    1620
tctatgtact gtaatagtgt gattactatg ctctagagaa aagtctaccc ctgctaagga    1680
gttctcatcc ctctgtcagg gtcagtaagg aaaacggtgg cctagggtac aggcaacaat    1740
gagcagacca acctaaattt ggggaaatta ggagaggcag agatagaacc tggagccact    1800
tctatctggg ctgttgctaa tattgaggag gcttgcccca cccaacaagc catagtggag    1860
agaactgaat aaacaggaaa atgccagagc ttgtgaaccc tgtttctctt gaagaactga    1920
ctagtgagat ggcctgggga agctgtgaaa gaaccaaaag agatcacaat actcaaaaga    1980
gagagagaga gaaaaaagag agatcttgat ccacagaaat acatgaaatg tctggtctgt    2040 ccacccatc aacaagtctt gaaacaagca acagatggat agtctgtcca aatggacata    2100
agacagacag cagtttccct ggtggtcagg gagggtttt ggtgataccc aagttattgg     2160
gatgtcatct tcctggaagc agagctgggg agggagagcc atcaccttga taatgggatg    2220
aatggaagga ggcttaggac tttccactcc tggctgagag aggaagagct gcaacgaat    2280 taggaagacc aagacacaga tcacccgggg cttacttagc ctacagatgt cctacgggaa    2340
cgtgggctgg cccagcatag ggctagcaaa tttgagttgg atgattgttt ttgctcaagg    2400
caaccagagg aaacttgcat acagagacag atatactggg agaaatgact ttgaaaacct    2460
ggctctaagg tgggatcact aagggatggg gcagtctctg cccaaacata agagaactc    2520 tggggagcct gagccacaaa aatgttcctt tattttatgt aaaccctcaa gggttataga    2580
ctgccatgct agacaagctt gtccatgtaa tattcccatg ttttaccct gccctgcct     2640 tgattagact cctagcacct ggctagtttc taacatgttt tgtgcagcac agttttaat    2700 aaatgcttgt tacattc                                                  2717

<210> SEQ ID NO 34
<211> LENGTH: 25
<212> TYPE: DNA
<213> ORGANISM: Artificial Sequence
<220> FEATURE:
<223> OTHER INFORMATION: synthetic antisense oligomer sequence

<400> SEQUENCE: 34
ggcaatcctt atctttgtga cagtc                                          25

<210> SEQ ID NO 35
<211> LENGTH: 20
<212> TYPE: DNA
<213> ORGANISM: Artificial Sequence
<220> FEATURE:
<223> OTHER INFORMATION: synthetic antisense oligomer sequence

<400> SEQUENCE: 35
tttgctgaag caatttgggg                                                20

<210> SEQ ID NO 36
<211> LENGTH: 23
```

```
<212> TYPE: DNA
<213> ORGANISM: Artificial Sequence
<220> FEATURE:
<223> OTHER INFORMATION: synthetic antisense oligomer sequence

<400> SEQUENCE: 36
gatccaggga tcttagctaa cgg                                      23

<210> SEQ ID NO 37
<211> LENGTH: 23
<212> TYPE: DNA
<213> ORGANISM: Artificial Sequence
<220> FEATURE:
<223> OTHER INFORMATION: synthetic antisense oligomer sequence

<400> SEQUENCE: 37
ttctcttccc aagacccatg agt                                      23
```